(12) United States Patent
Nishio et al.

(10) Patent No.: US 9,056,095 B2
(45) Date of Patent: Jun. 16, 2015

(54) IMMUNOGENIC COMPOSITION

(75) Inventors: Reiji Nishio, Kamakura (JP); Nobuo Ida, Kamakura (KP)

(73) Assignee: Toray Industries, Inc. (JP)

( * ) Notice: Subject to any disclaimer, the term of this patent is extended or adjusted under 35 U.S.C. 154(b) by 152 days.

(21) Appl. No.: 13/202,336

(22) PCT Filed: Feb. 26, 2010

(86) PCT No.: PCT/JP2010/053055
§ 371 (c)(1),
(2), (4) Date: Aug. 19, 2011

(87) PCT Pub. No.: WO2010/098432
PCT Pub. Date: Sep. 2, 2010

(65) Prior Publication Data
US 2011/0300223 A1 Dec. 8, 2011

(30) Foreign Application Priority Data
Feb. 27, 2009 (JP) .................................. 2009-045555

(51) Int. Cl.
*A61K 39/395* (2006.01)
*A61K 39/39* (2006.01)
*A61K 47/48* (2006.01)
*A61K 39/00* (2006.01)

(52) U.S. Cl.
CPC ........... *A61K 39/39* (2013.01); *A61K 47/48215* (2013.01); *A61K 47/4823* (2013.01); *A61K 2039/545* (2013.01); *A61K 2039/55555* (2013.01); *A61K 2039/6025* (2013.01)

(58) Field of Classification Search
None
See application file for complete search history.

(56) References Cited

FOREIGN PATENT DOCUMENTS

| | | |
|---|---|---|
| EP | 1 857 489 A1 | 11/2007 |
| EP | 2 336 173 A1 | 6/2011 |
| JP | 2001-503254 A | 3/2001 |
| JP | 2008-088158 A | 4/2008 |
| WO | 2006/095668 A1 | 9/2006 |

OTHER PUBLICATIONS

Singh et al. Nature Biotechnology, 1999, vol. 17, p. 1075-1081.*
Tatsuro Ouchi, et al., "Modification of polylactide upon physical properties by solution-cast blends from polylactide and polylactide-grafted Dextran", *Polymer*, vol. 44, pp. 3927-3933, 2003.
S.J. de Jong, et al., "Novel self-assembled hydrogels by stereocomplex formation in aqueous solution of enantiomeric lactic acid oligomers grafted to dextran", *Macromolecules*, 2000, vol. 33, pp. 3680-3686, American Chemical Society.
Phillip Gribbon, et al., "Macromolecular diffusion of biological polymers measured by confocal fluorescence recovery after photobleaching", Aug. 1998, vol. 75, pp. 1032-1039, pp. 1032-1039, *Biophysical Journal*, Biophysical Society.
Ya-Ping Li, et al., "PEGylated PLGA nanoparticles as protein carriers: synthesis, preparation and biodistribution in rats", 2001, *Journal of Controlled Release*, vol. 71, pp. 203-211.
Shirui Mao, et al., "Effect of WOW process parameters on morphology and burst release of FITC-dextran loaded PLGA microphores", 2007, *International Journal of Pharmaceutics*, vol. 334, pp. 137-148.
Ulf Schröder et al., "Crystallized Dextran Nanospheres with Entrapped Antigen and Their Use as Adjuvants," *Journal of Immunological Methods*, vol. 70, No. 1, 1984, pp. 127-132.
M. Tobío et al., "Stealth PLA-PEG Nanoparticles as Protein Carriers for Nasal Administration," *Pharmaceutical Research*, vol. 15, No. 2, 1998, pp. 270-275.
Alejandro Sánchez et al., "Formulation strategies for the stabilization of tetanus toxoid in poly(lactide-co-glycolide) microspheres," International Journal of Pharmaceutics, vol. 185, No. 2, 1999, pp. 255-266.
X.M. Deng et al., "Optimization of preparative conditions for poly-DL-lactide-polyethylene glycol microspheres with entrapped *Vibrio cholera* antigens," Journal of Controlled Release, vol. 58, No. 2, 1999, pp. 123-131.
Carmen Arigita et al., "Immunogenicity of meningococcal PorA formulations encapsulated in biodegradable microspheres," European Journal of Pharmaceutical Sciences, vol. 21, No. 2-3, 2004, pp. 131-141.
Wenlei Jiang et al., "Biodegradable poly(lactic-co-glycolic acid) microparticles for injectable delivery of vaccine antigens," Advanced Drug Delivery Reviews, vol. 57, 2005, pp. 391-410.
Xue-Qing Zhang et al., "A Comparative Study of the Antigen-Specific Immune Response Induced by Co-Delivery of CpG ODN and Antigen Using Fusion Molecules or Biodegradable Microparticles," Journal of Pharmaceutical Sciences, vol. 96, No. 12, Dec. 2007, pp. 3283-3292.
S. Abolghasem Sajadi Tabassi et al., "Induction of high antitoxin titers against tetanus toxoid in rabbits by intranasal immunization with dextran microspheres," International Journal of Pharmaceutics, vol. 360, No. 1-2, 2008, pp. 12-17.
Qiang Wei et al., "Preparation of uniform-sized PELA microspheres with high encapsulation efficiency of antigen by premix membrane emulsification," Journal of Colloid and Interface Science, vol. 323, No. 2, 2008, pp. 267-273.

* cited by examiner

*Primary Examiner* — Yunsoo Kim
(74) *Attorney, Agent, or Firm* — DLA Piper LLP (US)

(57) ABSTRACT

An immunogenic composition includes as an effective ingredient an antigen-adjuvant microparticle complex containing an antigen encapsulated in an adjuvant microparticle composed of an amphiphilic polymer(s) whose hydrophobic segment is a poly(hydroxy acid), or a particle composed of the antigen-adjuvant microparticle complex associated together, can induce a high immune response against the antigen even with a small amount of the antigen and a small number of doses, so that the immunogenic composition is useful as a vaccine effective for therapy and prophylaxis of infectious diseases, cancer and the like.

19 Claims, 6 Drawing Sheets

IMMUNOGENIC COMPOSITION

RELATED APPLICATIONS

This is a §371 of International Application No. PCT/JP2010/053055, with an international filing date of Feb. 26, 2010 (WO 2010/098432 A1, published Sep. 2, 2010), which is based on Japanese Patent Application No. 2009-045555, filed Feb. 27, 2009, the subject matter of which is incorporated by reference.

TECHNICAL FIELD

This disclosure relates to an immunogenic composition comprising as an effective ingredient an antigen-adjuvant microparticle complex containing an antigen encapsulated in an adjuvant microparticle composed of an amphiphilic polymer(s).

BACKGROUND

For enhancement of the immune-activating capacity of an antigen, an adjuvant is used together with the antigen. Although complete Freund's adjuvant (CFA) is known to have an excellent effect as an adjuvant, CFA is composed of killed bacteria and an oil emulsion, and hence has strong side effects such as strong inflammatory reaction and formation of ulcerative swelling (granuloma) at the administration site. Therefore, use of CFA for human is not permitted in view of safety. Adjuvants whose administration to human is permitted are limited. Examples of the adjuvants whose administration to human is permitted include aluminum hydroxide adjuvants, but their immune-activating capacities are not necessarily sufficient and hence they need to be repeatedly administered to allow acquisition of immunity. Therefore, development of an immunogenic composition using an efficient and strong adjuvant, which composition can be used for human, has been demanded.

For development of a novel adjuvant aiming to attain a high immune-activating capacity, a method wherein an antigen is encapsulated in a microparticle has been attempted. It has been reported that administration of a microparticulated antigen enhances immunological reactions such as antibody production compared to the case of administration of an antigen alone, but the effect of its administration is not necessarily high, and only an effect at almost the same level as in the case of the above-mentioned aluminum hydroxide adjuvant has been reported. This is considered to be due to difficulty in efficient encapsulation of hydrophilic antigen molecules such as protein in microparticles studied so far, such as microparticles comprising hydrophobic polylactic acid-polyglycolic acid copolymers, while maintaining the structures of the antigen molecules (Advanced Drug Delivery Reviews, 2005, Vol. 57, pp. 391-410).

In recent years, a novel microparticle technology has been reported (WO 2006/095668 A1 and JP 2008-088158 A), which technology uses an amphiphilic polymer and enables highly efficient encapsulation of a high molecular protein. Although this novel microparticle has been studied for its sustained-release performance for drugs, its adjuvant function in cases where an antigen is encapsulated therein has not been studied at all. Further, in terms of the mechanism by which a microparticle containing an antigen functions as an adjuvant, it is thought that the function for sustained release of the antigen molecule as well as the mechanism by which the microparticle containing an antigen is incorporated in its entirety into an immunocyte and releases the antigen in the cell are important, and it is further thought that the function of drug release from the particle and the performance as an adjuvant are not necessarily correlated with each other. Therefore, it is difficult to infer the adjuvant function from the sustained-release performance of the particle, and an effective adjuvant having a much better performance than aluminum adjuvants has not been realized so far by conventional technologies using microparticles in spite of the demand for its development.

It could therefore be helpful to provide an immunogenic composition which has a high immune-activating capacity even with a small antigen amount and/or a small number of doses.

SUMMARY

We studied a method by which a high level of immune activation can be induced using a small amount of antigen and with a small number of doses thereof and, as a result, discovered that an antigen-adjuvant microparticle complex containing an antigen encapsulated in an adjuvant microparticle has a high immune-activating capacity in vivo. That is, we provide:

(1) An immunogenic composition comprising as an effective ingredient an antigen-adjuvant microparticle complex containing an antigen encapsulated in an adjuvant microparticle composed of an amphiphilic polymer(s) whose hydrophobic segment is a poly(hydroxy acid).

(2) The immunogenic composition according to (1), comprising as an effective ingredient a particle composed of the antigen-adjuvant microparticle complex associated together.

(3) The immunogenic composition according to (1) or (2), wherein the adjuvant microparticle has a hydrophilic portion in the inside thereof, the hydrophilic portion being composed of a hydrophilic segment of the amphiphilic polymer, and has an outer layer composed of a hydrophobic portion constituted by the hydrophobic segment of the amphiphilic polymer.

(4) The immunogenic composition according to any of (1) to (3), wherein the hydrophilic segment of the amphiphilic polymer is a polysaccharide or a polyethylene glycol.

(5) The immunogenic composition according to any of (1) to (4), wherein the amphiphilic polymer is a graft amphiphilic polymer composed of a polysaccharide backbone and a poly(hydroxy acid) graft chain.

(6) The immunogenic composition according to (4) or (5), wherein the polysaccharide is dextran.

(7) The immunogenic composition according to any of (1) to (4), wherein the amphiphilic polymer is a block polymer composed of a poly(hydroxy acid) and a polyethylene glycol.

(8) The immunogenic composition according to any of (1) to (7), wherein the poly(hydroxy acid) is a poly(lactic-co-glycolic acid).

(9) The immunogenic composition according to any of (1) to (8), further comprising a surface modifier bound to the poly(hydroxy acid) of the adjuvant microparticle.

(10) The immunogenic composition according to any of (1) to (9), wherein the average particle size of the antigen-adjuvant microparticle complex or the particle composed of the antigen-adjuvant microparticle complex associated together is 0.1 to 50 µm.

(11) The immunogenic composition according to any of (1) to (10), further comprising an immune-activating substance.

(12) The immunogenic composition according to (11), wherein the immune-activating substance is a nucleic acid.
(13) The immunogenic composition according to (11) or (12), wherein the immune-activating substance is CpG.

An immunogenic composition with which stronger immune activation than before is now possible in vivo.

DETAILED DESCRIPTION

Figure 1:
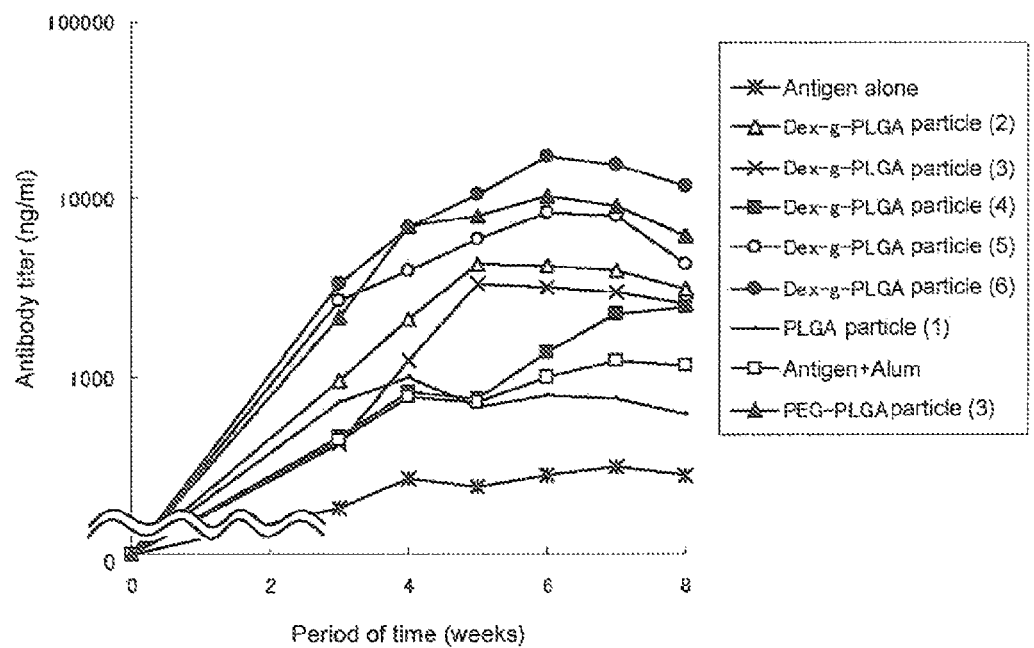
FIG. 1 shows immunological evaluation 1 of OVA-containing immunogenic compositions.

We provide an immunogenic composition comprising an antigen-adjuvant microparticle complex containing an antigen encapsulated in an adjuvant microparticle composed of an amphiphilic polymer(s) whose hydrophobic segment is a poly(hydroxy acid).

First, the amphiphilic polymer constituting the adjuvant microparticle is described. Being "amphiphilic" means that properties of both hydrophilicity and hydrophobicity are retained. When solubility of a certain portion in water is higher than those of other portions, the portion is said to be hydrophilic. The hydrophilic portion is preferably soluble in water, but even in cases where the portion has poor solubility in water, it is sufficient if the solubility in water is higher than those of other portions. When solubility of a certain portion in water is lower than those of other portions, the segment is said to be hydrophobic. The hydrophobic portion is preferably insoluble in water, but even in cases where the portion is soluble in water, it is sufficient if the solubility in water is lower than those of other portions.

The amphiphilic polymer means a polymer having the above-mentioned amphiphilicity as the whole molecule. The polymer means that the molecule has a molecular structure wherein the hydrophilic segment or the hydrophobic segment of the amphiphilic polymer, or the both, is/are constituted by a structure(s) in which minimum units (monomers) are repeated. The amphiphilic polymer may have a structure having a hydrophilic segment(s) and a hydrophobic segment(s), and may be a linear block polymer having a hydrophilic segment(s) and a hydrophobic segment(s) linked to each other; a branched polymer having a branch(es) in which one or both of a hydrophilic segment(s) and a hydrophilic segment(s) exist(s); or a graft polymer in which plural hydrophobic segments are grafted to a hydrophilic segment or plural hydrophilic segments are grafted to a hydrophobic segment. The amphiphilic polymer is preferably a polymer having one hydrophilic segment, most preferably a linear block polymer having one each of a hydrophilic segment and a hydrophobic segment, or a graft polymer having plural hydrophobic segments grafted on a hydrophilic segment backbone.

The amphiphilic polymer constituting the immunogenic composition may be a set of plural types of amphiphilic polymers composed of constituent polymers having different hydrophilic portions and/or hydrophilic portions, or a set of amphiphilic polymers having the same constituent polymers but having plural types of linking patterns, as long as the amphiphilic polymer has properties as an adjuvant microparticle. In view of achievement of stable performance and enhancement of productivity, the amphiphilic polymer is preferably a set of a small number of types of amphiphilic polymers, more preferably a set of mainly not more than 2 types of amphiphilic polymers, and still more preferably constituted by mainly a single type of amphiphilic polymer.

The hydrophobic segment of the amphiphilic polymer is a poly(hydroxy acid). The poly(hydroxy acid) is not restricted, and preferably a biocompatible polymer which does not have a severely adverse effect upon administration to a living body. The biocompatibility herein means that LD50 in the case of oral administration of the polymer to rats is not less than 2,000 mg/kg. Further, the polymer may be a copolymer of plural types of hydroxy acids, and is preferably a polymer of not more than 2 types of hydroxy acids. Particular preferred examples of the poly(hydroxy acid) include polyglycolic acid, polylactic acid, poly(2-hydroxybutyric acid), poly(2-hydroxyvaleric acid), poly(2-hydroxycaproic acid), poly(2-hydroxycaproic acid) and poly(malic acid); and derivatives and copolymers of these macromolecular compounds; among which polylactic acid, polyglycolic acid, and poly(lactic-co-glycolic acid) copolymers are more preferred. Further, in cases where the poly(hydroxy acid) is a poly(lactic-co-glycolic acid), the composition ratio of the poly(lactic-co-glycolic acid) (lactic acid/glycolic acid) (mol/mol %) is not restricted, and the ratio is preferably 100/0 to 30/70, more preferably 60/40-40/60.

The hydrophilic segment of the amphiphilic polymer is not restricted, and preferably a biocompatible polymer, as in the case of the hydrophobic segment. Further, to give a persistent adjuvant capacity to the adjuvant microparticle composed of an amphiphilic polymer, the segment is preferably a refractory polymer which is not easily decomposed in a living body or cell of a mammal or bird. Particular examples of the biocompatible and refractory polymer include polyethylene glycol, polyvinyl pyrrolidone, polyvinyl alcohol, polyethyleneimine, polyacrylic acid, polymethacrylic acid, poly-1,3-dioxolane, 2-methacryloyloxyethyl phosphoryl choline polymer, poly-1,3,6-trioxane, polyamino acid and refractory polysaccharides (e.g., cellulose, chitin, chitosan, gellan gum, alginic acid, hyaluronic acid, pullulan and dextran). In cases where the hydrophilic segment is polyethylene glycol, polyvinyl pyrrolidone, polyvinyl alcohol, polyethyleneimine, polyacrylic acid, polymethacrylic acid, poly-1,3-dioxolane, 2-methacryloyloxyethyl phosphoryl choline polymer, poly-1,3,6-trioxane or polyamino acid, the amphiphilic polymer is preferably a linear block polymer having one each of a hydrophilic segment and a hydrophobic segment and, in cases where the hydrophilic segment is a polysaccharide, the amphiphilic polymer is preferably a graft polymer having plural hydrophobic segments grafted on a hydrophilic segment backbone. Further, the hydrophilic segment of the amphiphilic polymer is preferably polyethylene glycol or a refractory polysaccharide, and the polysaccharide is more preferably dextran.

The amphiphilic polymer having a hydrophobic segment(s) composed of poly(hydroxy acid) and a hydrophilic segment(s) preferably has water immiscibility as the whole polymer, in view of antigen-encapsulation capacity and persistency upon administration to a living body.

The average molecular weight of the hydrophilic segment of the amphiphilic polymer is not restricted and, in the case of a block polymer wherein a hydrophilic segment(s) and a hydrophilic segment(s) are linearly linked to each other, the average molecular weight is preferably 1,000 to 50,000, more preferably 2,000 to 15,000. The term "block" herein means a portion in a polymer molecule, which portion is composed of not less than 5 monomer units and different from the other adjacent portion(s) in terms of the chemical structure or the configuration. A polymer constituted by at least two blocks linearly linked to each other is called a block polymer. Each block itself constituting the block polymer may be a random, alternating or gradient polymer composed of not less than 2 types of monomer units. The block polymer is preferably constituted by one each of a polymer forming a hydrophilic segment and a polyhydroxy acid.

In the case of a graft polymer having a hydrophobic segment(s) grafted on a hydrophilic segment backbone, the average molecular weight of the hydrophilic segment is preferably 1,000 to 100,000, more preferably 2,000 to 50,000, still more preferably 10,000 to 40,000. The number of the graft chains is preferably 2 to 50. The number of the graft chains can be calculated based on the ratio between the hydrophilic segment backbone and the hydrophobic segment backbone; the average molecular weight of the hydrophobic segment; and the average molecular weight of the hydrophilic segment backbone used; which are obtained by $^1$H-NMR measurement.

The preferred average molecular weight ratio between the hydrophobic segment and the hydrophilic segment varies depending on the amphiphilic polymer and, in the case of a block polymer wherein a hydrophobic segment(s) and a hydrophilic segment(s) are linearly bound to each other, the average molecular weight ratio between the hydrophilic segment(s) and the hydrophobic segment(s) is preferably not less than 1:1, more preferably not less than 1:2, still more preferably not less than 1:4, especially preferably not less than 1:4 and not more than 1:25.

Preferably, in the case of a graft polymer having plural hydrophobic segments grafted on a hydrophilic segment backbone, the average molecular weight ratio between the hydrophilic segment backbone portion and the whole hydrophobic segment graft chains is not less than 1:3 and the average molecular weight of each graft chain is 2,500 to 40,000. More preferably, the overall average molecular weight ratio is not less than 1:5 and the average molecular weight of each graft chain is 5,000 to 40,000.

It should be noted that the above-mentioned average molecular weight is a number average molecular weight, unless otherwise specified. The number average molecular weight is an average molecular weight calculated without weighting by the molecular size, and the number average molecular weights of the amphiphilic polymer and the polymers constituting the hydrophilic segment(s) of the amphiphilic polymer can be calculated as molecular weights in terms of polystyrene and pullulan measured by gel permeation chromatography (GPC). Further, the average molecular weight of poly(hydroxy acid) can be calculated by measurement by nuclear magnetic resonance (NMR), based on the ratio between the peak integration value for terminal residues and the peak integration value for the others.

The amphiphilic polymer may be synthesized by a known method, and examples of the method include a method wherein a poly(hydroxy acid) polymer is added to a polymer to be used as a hydrophilic segment and condensation reaction is carried out with the resulting mixture to produce an amphiphilic polymer; a method wherein hydroxy acid-activated monomers are added to a polymer to be used as a hydrophilic segment and polymerization reaction is carried out with the resulting mixture to produce an amphiphilic polymer; and a method wherein, conversely, monomers for constituting a hydrophilic segment are added to a hydrophobic segment which is a poly(hydroxy acid) polymer and polymerization reaction is carried out with the resulting mixture to produce an amphiphilic polymer.

For example, an amphiphilic polymer constituted by polyethylene glycol and poly(hydroxy acid) can be produced by a method in which hydroxy acid-activated monomers are added to polyethylene glycol in the presence of a tin catalyst, and polymerization reaction is carried out with the resulting mixture for introduction of the poly(hydroxy acid), thereby producing an amphiphilic block polymer (Journal of Controlled Release, 71, p. 203-211 (2001)).

Further, for example, a graft-type amphiphilic polymer constituted by a polysaccharide and a poly(hydroxy acid) graft chain(s) can be produced as described in (1), (2) or (3) below:

(1) a method wherein, in the presence of a tin catalyst, hydroxy acid-activated monomers are added to a polysaccharide and polymerization reaction is carried out, thereby introducing poly(hydroxy acid), to produce a graft-type amphiphilic polymer (Macromolecules, 31, p. 1032-1039 (1998));

(2) a method wherein unprotected hydroxyl groups in a part of a polysaccharide in which most of its hydroxyl groups are protected by substituents are activated by a base, and hydroxy acid-activated monomers are added thereto to introduce a graft chain(s) composed of poly (hydroxy acid), followed by finally removing the protecting groups, thereby producing a graft-type amphiphilic polymer (Polymer, 44, p. 3927-3933, (2003)); and (3) a method wherein condensation reaction of a copolymer of poly(hydroxy acid) with a polysaccharide is carried out using a dehydrating agent and/or a functional-group-activating agent, thereby producing a graft-type amphiphilic polymer (Macromolecules, 33, p. 3680-3685 (2000)).

The adjuvant microparticle is described below. The adjuvant microparticle is a microparticle having an adjuvant capacity, and the adjuvant capacity means a capacity with which the immune response upon administration of an antigen to a living body can be caused at a higher level than in the case of administration of the antigen alone. Further, the adjuvant microparticle is a microparticle composed of an amphiphilic polymer, and an antigen is encapsulated in the adjuvant microparticle to form an antigen-adjuvant microparticle complex, which is an effective ingredient of the immunogenic composition.

The structure of the adjuvant microparticle is not restricted, and a structure wherein the hydrophilic segment of the amphiphilic polymer is included in the adjuvant microparticle and the hydrophobic segment of the amphiphilic polymer is contained as an outer layer is preferred in view of stable maintenance of the encapsulated antigen. The method of production of an adjuvant microparticle having such a structure is not restricted, and examples of the production method include a method comprising: (a) the step of mixing an aqueous solvent A with a water-immiscible organic solvent B in which an amphiphilic polymer is dissolved, to form a reversed-phase emulsion; and (b) the step of removing the solvent from the reversed-phase emulsion to obtain an adjuvant microparticle. In this process, by inclusion of an antigen in the aqueous solvent A, an antigen-adjuvant microparticle complex wherein the antigen is encapsulated can be constituted. The steps (a) and (b) are described below.

As the aqueous solvent A in the step (a), water, or an aqueous solution containing a water-soluble component is used. Examples of the water-soluble component include inorganic salts, sugars, organic salts and amino acids.

The water-immiscible organic solvent B in the step (a) is preferably a solvent in which the poly(hydroxy acid) of the amphiphilic polymer is soluble and the polymer constituting the hydrophilic segment is poorly soluble or insoluble, and, preferably, the solvent can be removed by vaporization by freeze drying. The solubility of the water-immiscible organic solvent B in water is preferably not more than 30 g (water-immiscible organic solvent B)/100 ml (water). Particular examples of the water-immiscible organic solvent B include ethyl acetate, isopropyl acetate, butyl acetate, dimethyl carbonate, diethyl carbonate, methylene chloride and chloroform.

The ratio between the water-immiscible organic solvent B and the aqueous solvent A is 1,000:1 to 1:1, preferably 100:1 to 1:1. The concentration of the amphiphilic polymer in the water-immiscible organic solvent B varies depending on the types of the water-immiscible organic solvent B and the amphiphilic polymer, and the concentration is 0.01 to 90% (w/w), preferably 0.1 to 50% (w/w), more preferably 1 to 20% (w/w).

In the step (a), in the process of formation of a reversed-phase emulsion with an aqueous solvent A and a water-immiscible organic solvent B in which an amphiphilic polymer is dissolved, the reversed-phase emulsion may be formed using, depending on the pharmaceutical purpose, a water-immiscible organic solvent B in which two or more types of amphiphilic polymers are dissolved.

In the step (a), to aid the formation of a reversed-phase emulsion and to form a uniform and fine reversed-phase emulsion, an additive may be added. The additive is preferably a compound selected from $C_3$-$C_6$ alkyl alcohols, $C_3$-$C_6$ alkyl amines and $C_3$-$C_6$ alkyl carboxylic acids. The structure of each alkyl chain in these additives is not restricted, and the alkyl chain may have either a linear structure or a branched structure, and may be either a saturated alkyl or an unsaturated alkyl. The additive is especially preferably tert-butanol, iso-propanol or pentanol.

In the step (b), the method of removal of the solvent from the reversed-phase emulsion is not restricted, and examples thereof include heating, drying under reduced pressure, dialysis, freeze drying, centrifugation, filtration and reprecipitation, and combinations thereof. Among the methods of removal of the solvent from the reversed-phase emulsion, freeze drying is preferred since it causes less structural change due to fusion of particles in the reversed-phase emulsion, or the like. The conditions and the apparatus for the freeze drying are those which allow inclusion of a freezing process and a drying step under reduced pressure, and the process of freeze drying especially preferably comprises prior freezing, primary drying under reduced pressure at low temperature, and secondary drying under reduced pressure, which are conventionally carried out in freeze drying. For example, in cases where a dispersion of an antigen-adjuvant microparticle complex in a water-immiscible solvent is to be obtained, the reversed-phase emulsion is cooled/frozen to not more than the melting points of the aqueous solvent A and the water-immiscible organic solvent B, and then dried under reduced pressure, to obtain freeze-dried adjuvant microparticles. The temperature for the prior freezing may be experimentally determined as appropriate depending on the solvent composition, and is preferably not more than −20° C. The degree of reduction of the pressure during the drying process may also be determined as appropriate depending on the solvent composition, and is preferably not more than 3,000 Pa, more preferably not more than 500 Pa, in view of shortening of the drying time. The freeze drying is preferably carried out using a freeze dryer for laboratory use which has a cold trap and can be connected to a vacuum pump, or a shelf-type vacuum freeze dryer used for production of pharmaceuticals or the like. After the prior freezing with liquid nitrogen, a cooling medium or the like, the drying under reduced pressure may be carried out with cooling or at room temperature using a vacuum device such as a vacuum pump.

The type of the antigen encapsulated in the adjuvant microparticle is not restricted, and may be a peptide, protein, glycoprotein, glycolipid, lipid, carbohydrate, nucleic acid or polysaccharide; or a virus, bacterial cell, allergenic substance, tissue or cell comprising these. Particular examples thereof include pollen-derived antigens, hepatitis A virus-derived antigens, hepatitis B virus-derived antigens, hepatitis C virus-derived antigens, hepatitis D virus-derived antigens, hepatitis E virus-derived antigens, hepatitis F virus-derived antigens, HIV virus-derived antigens, influenza virus-derived antigens, herpes virus (HSV-1, HSV-2)-derived antigens, anthrax-derived antigens, chlamydia-derived antigens, pneumococcus-derived antigens, Japanese encephalitis virus-derived antigens, measles virus-derived antigens, rubella virus-derived antigens, *Clostridium tetani*-derived antigens, chickenpox virus-derived antigens, SARS virus-derived antigens, EB virus-derived antigens, papilloma virus-derived antigens, *Helicobacter pylori*-derived antigens, rabies virus-derived antigens, West Nile virus-derived antigens, hantavirus-derived antigens, *Streptococcus*-derived antigens, *Staphylococcus*-derived antigens, *Bordetella pertussis*-derived antigens, *Mycobacterium tuberculosis*-derived antigens, *Plasmodium*-derived antigens, poliovirus-derived antigens, antigens derived from various zoonotic infections, cancer antigens, and antigens derived from various food allergies.

The encapsulated antigen does not need to be a single antigen. An immune response may be induced against cancer cells, bacteria, viruses or the like which are constituted by plural constituents. In such cases, the antigen may be plural types of proteins or the like which may cause immune responses, or a mixture of substances whose types cannot be specified. Further, inclusion of plural types of antigens for positively inducing immune responses against the plural types of antigens is one of the modes of use of the immunogenic composition. Preferably not less than 3 types, more preferably a single type of an antigen(s) is/are encapsulated in the adjuvant microparticle.

The antigen-adjuvant microparticle complex may change the retention capacity of the antigen depending on the type(s) of the polymer(s) constituting the adjuvant microparticle and the preparation method. The mechanism by which the immunogenicity is provided by the antigen-adjuvant microparticle complex may include plural processes, such as a process wherein the antigen released from the adjuvant microparticle is recognized by immunocompetent cells, and a process wherein the adjuvant microparticle itself is recognized by immunocompetent cells. An excellent effect can be obtained also by the synergistic effect of these processes.

The type of the immune response induced by the process in which the antigen-adjuvant microparticle complex makes immunocompetent cells recognize the antigen varies depending on the type of the process, and a preferred process may be selected depending on the type of the immune response to be induced and the site of administration. That is, the antigen does not necessarily need to be released from the antigen-adjuvant microparticle complex, and the mode with which the optimum immunogenicity of interest is realized is attained by optimization depending on the antigen and the type of the immune response to be activated in a preferred method of use thereof. However, in cases where the antigen is extremely quickly released from the antigen-adjuvant microparticle complex, a long-term continuous immune-activating action, which is an excellent property, cannot be obtained, so that preferably not less than 10% of the antigen in the antigen-adjuvant microparticle complex is still retained in the living body as the complex one week after the administration, and more preferably not less than 50% of the antigen is still encapsulated one week after the administration. These release behaviors can be confirmed, as shown in Examples, by in vitro evaluation mimicking the in vivo environment.

The antigen-adjuvant microparticle complex attains a good effect as an effective component of the immunogenic composition even in a particle state wherein the complex is associated. The term "association" herein means that two or more particles are bound together by an interparticle force or via another substance, to form an aggregate. The interparticle force is not restricted, and examples thereof include the hydrophobic interaction, hydrogen bond, van der Waals force and the like. The association is not restricted to the state wherein the microparticles are in contact with each other, and a substance having an affinity to the microparticles may exist between the microparticles, or the microparticles may be dispersed in a matrix. As the substance having an affinity to the microparticles, or the matrix, a polymer is preferred, and an amphiphilic polymer whose hydrophobic portion is poly(hydroxy acid) and which has the same constituent as that of the adjuvant microparticle is more preferred. Particular examples thereof include amphiphilic polymers each composed of a polysaccharide backbone and a poly(hydroxy acid) graft chain(s), block polymers each composed of polyethylene glycol and poly(hydroxy acid), and poly(hydroxy acid).

The association of the antigen-adjuvant microparticle complex may be either in a state where the complexes are reisolated upon their use, or may be in a state where they are not reisolated upon their use. It should be noted that, even in cases where the shape of the particle formed by association of the antigen-adjuvant microparticle complex is in a state from which the association of the complex cannot be known, the particle is considered to have been formed by association of the complex as long as the production process of the particle comprises a step of associating the complex.

The step of associating the complexes is not restricted, and particular examples thereof include a step of introducing the antigen-adjuvant microparticle complex or an antigen-adjuvant microparticle complex dispersion to a liquid phase C containing a surface modifier to remove the disperse medium, thereby causing association. This step is described below.

In cases where the antigen-adjuvant microparticle complex is dispersed in a disperse medium to prepare a dispersion of the complex, the disperse medium is not restricted, and in cases where the adjuvant microparticle has a hydrophilic portion in the inside thereof, the hydrophilic portion being composed of a hydrophilic segment of an amphiphilic polymer, and has an outer layer comprising a hydrophobic portion composed of a hydrophobic segment of an amphiphilic polymer, the disperse medium is preferably a solvent in which poly(hydroxy acid) of the amphiphilic polymer is soluble and the polymer constituting the hydrophilic segment is substantially insoluble, for the purpose of protecting the structure of the adjuvant microparticle. In this case, the solvent may be either a water-immiscible organic solvent or a water-miscible organic solvent. Particular examples of the solvent in which the poly(hydroxy acid) of the amphiphilic polymer is soluble and the polymer constituting the hydrophilic segment is substantially insoluble include ethyl acetate, isopropyl acetate, butyl acetate, dimethyl carbonate, diethyl carbonate, methylene chloride, chloroform, dioxane, toluene and xylene.

Preferably, the liquid phase C is one in which a surface modifier is soluble, and has a higher boiling point than the disperse medium. The liquid phase C may be any of an aqueous solvent, water-immiscible organic solvent and water-miscible organic solvent. As the aqueous solvent, water or an aqueous solution containing a water-soluble component is preferred, and examples of the water-soluble component include inorganic salts, sugars, organic salts and amino acids. Examples of the water-immiscible organic solvent include silicone oil, sesame oil, soybean oil, corn oil, cottonseed oil, coconut oil, linseed oil, mineral oil, castor oil, hydrogenated castor oil, liquid paraffin, n-hexane, n-heptane, glycerol and oleic acid. Examples of the water-miscible organic solvent include glycerin, acetone, ethanol, acetic acid, dipropylene glycol, triethanolamine and triethylene glycol. Among these, the liquid phase C is preferably an aqueous solvent or a water-miscible organic solvent. In cases where the liquid phase C is an aqueous solvent and the disperse medium is a water-immiscible organic solvent, the obtained suspension of an antigen-adjuvant microparticle complex is in the form of the so called solid-in-oil-in-water (S/O/W) emulsion and, in cases where the liquid phase C is a water-immiscible organic solvent or a water-miscible organic solvent, and immiscible in the disperse medium, the suspension is in the form of a solid-in-oil-in-oil (S/O1/O2) emulsion.

The surface modifier is preferably a compound which stabilizes the water-oil interface of the S/O/W emulsion or the oil-oil interface of the S/O1/O2 emulsion, which compound has a property to enhance the colloidal stability of the particle formed by association of the antigen-adjuvant microparticle complex. The enhancement of the colloidal stability herein means prevention or delaying of aggregation, in the solvent, of the particles formed by association of the antigen-adjuvant microparticle complex. The surface modifier may be a single agent or a mixture of plural agents.

The surface modifier is preferably a hydrophilic polymer or an amphiphilic compound.

The hydrophilic polymer as the surface modifier is preferably polyethylene glycol, polyvinyl pyrrolidone, polyvinyl alcohol, polyethyleneimine, polyacrylic acid, polymethacrylic acid, poly-1,3-dioxolane, 2-methacryloyloxyethyl phosphoryl choline polymer, poly-1,3,6-trioxane, polyamino acid, peptide, protein or sugar polysaccharide, or an analogue of any of these. Examples of the analogue of the hydrophilic polymer include, but are not limited to, surfactants prepared from hydrophilic polymers by, for example, partial modification of hydrophobic groups such as long-chain alkyl.

The polyethylene glycol analogue as the surface modifier is preferably "Pluronic" (registered trademark of BASF) commercially available from BASF, or its equivalent.

The polyamino acid as the surface modifier is preferably polyaspartic acid or polyglutamic acid, or its analogue. Analogues prepared by introducing long-chain alkyl to a part of polyaspartic acid or polyglutamic acid are more preferred.

Examples of the peptide as the surface modifier include basic peptides, and the protein as the surface modifier is preferably gelatin, casein or albumin in view of enhancement of dispersibility. Preferred examples of the protein also include antibodies.

The sugar as the surface modifier is preferably a monosaccharide, oligosaccharide or polysaccharide. The polysaccharide is preferably cellulose, chitin, chitosan, gellan gum, alginic acid, hyaluronic acid, pullulan or dextran, and cholesterol-bearing pullulan is especially preferred in view of enhancement of the dispersibility of the particle. An analogue of any of cellulose, chitin, chitosan, gellan gum, alginic acid, hyaluronic acid, pullulan and dextran is preferred.

The peptide, protein or sugar as the surface modifier is especially preferably an analogue prepared by, for example, partial modification of hydrophobic groups such as long-chain alkyl, or an analogue prepared by modifying the above-mentioned hydrophilic polymer or amphiphilic compound.

Examples of the amphiphilic compound as the surface modifier include lipids and surfactants. Preferred examples of the surfactants include nonionic surfactants such as polyoxyethylene polypropylene glycol copolymers, sucrose fatty acid esters, polyethylene glycol fatty acid esters, polyoxyethylene sorbitan monofatty acid ester, polyoxyethylene sorbitan difatty acid ester, polyoxyethylene glycerol monofatty acid ester, polyoxyethylene glycerol difatty acid ester, polyglycerol fatty acid ester, polyoxyethylene castor oil and polyoxyethylene hydrogenated castor oil; alkyl sulfates such as sodium lauryl sulfate, ammonium lauryl sulfate and sodium stearyl sulfate; and lecithin.

The volume ratio between the disperse medium in which the antigen-adjuvant microparticle complex is dispersed and the liquid phase C is 1,000:1 to 1:1,000, preferably 100:1 to 1:100. The association number of the antigen-adjuvant microparticle complex obtained varies depending on this volume ratio and, as the ratio of the lipid phase C increases, a dispersion, in water, of particles produced by association of a larger number of the antigen-adjuvant microparticle complex is obtained, while, as the ratio of the lipid phase C decreases, the association number decreases. In cases where the ratio of the liquid phase C is smaller than a solution ratio of 1:4, most of the particles in the dispersion in water are each constituted by a single antigen-adjuvant microparticle complex. Thus, by controlling the volume ratio of the liquid phase C in the series of processes for production of the particle formed by association of the antigen-adjuvant microparticle complex, the antigen-adjuvant microparticle complex and the particle formed by association of the complex can be selectively prepared.

When the disperse medium containing the antigen-adjuvant microparticle complex is mixed with the liquid phase C, a stirring device such as a magnetic stirrer, turbine stirrer, homogenizer, membrane emulsification apparatus equipped with a porous membrane, or the like may be used as required.

The liquid phase C may contain, in addition to the surface modifier, various additives such as a buffer, antioxidant, salt, polymer and/or sugar depending on the pharmaceutical purpose. Further, the disperse medium in which the antigen-adjuvant microparticle complex is to be dispersed may contain various additives soluble in the disperse medium, such as an acidic compound, basic compound, amphiphilic polymer and/or biodegradable polymer, for the purpose of controlling the release rate of the encapsulated antigen by degradation or disintegration of the complex.

Further, an emulsifying operation of the formed solid-in-oil-in-water (S/O/W) emulsion or solid-in-oil-in-oil (S/O1/O2) emulsion may be carried out for the purpose of producing a finer particle formed by association of the antigen-adjuvant microparticle complexes. The method of emulsification is not restricted as long as a stable emulsion can be prepared thereby, and examples thereof include methods by stirring and methods using a high-pressure homogenizer, high-speed homomixer or the like.

In cases where the antigen-adjuvant microparticle complex is once dispersed in the disperse medium, and the obtained dispersion is added to the liquid phase C containing the surface modifier, a suspension of the particle formed by association of the desired adjuvant microparticle can be obtained by removal of the disperse medium. The method of removal of the disperse medium is not restricted, and examples thereof include solvent evaporation, dialysis, freeze drying, centrifugation, filtration and reprecipitation, among which solvent evaporation and freeze drying are especially preferred. In cases where an aqueous solvent was used as the liquid phase C, an aqueous dispersion of the particle formed by association of antigen-adjuvant microparticle complex can be obtained by this step.

Preferably, the surface modifier is bound to the antigen-adjuvant microparticle complex or the particle formed by association of the antigen-adjuvant microparticle complex. The binding herein may be either a non-covalent bond or covalent bond. The non-covalent bond is preferably a hydrophobic interaction, and may also be an electrostatic interaction, hydrogen bond or van der Waals force, or a combination of these bonds. In the non-covalent bond, poly(hydroxy acid) of the microparticle containing an amphiphilic polymer is preferably bound to the hydrophobic portion of the surface modifier by a hydrophobic interaction and, in this case, the disperse medium for the antigen-adjuvant microparticle complex in the microparticle dispersion is preferably water, buffer, physiological saline, aqueous surface modifier solution or hydrophilic solvent.

The average particle size of the antigen-adjuvant microparticle complex or the particles formed by association of the complex is preferably 0.1 to 50 µm, more preferably 0.1 to 10 µm. In particular, the average particle size of the antigen-adjuvant microparticle complex is preferably 0.1 to 1 µm, more preferably 0.1 to 0.5 µm, and the average particle size of the antigen-adjuvant microparticle complex is preferably 0.1 to 50 µm, more preferably 0.1 to 10 µm, still more preferably 1 to 10 µm. The average particle size of the antigen-adjuvant microparticle complex or the particle formed by association of the complex can be directly measured using image analysis by a scanning electron microscope (SEM: e.g., S-4800 manufactured by Hitachi, Ltd.).

The immunogenic composition may induce an immune response in a living body, and contains the antigen-adjuvant microparticle complex as an immunogenic substance. The type of the immune response which is induced by the immunogenic composition is not restricted. Examples of the type of the immune response to be induced include the Th1 immune response and the Th2 immune response, and it is known that one of these immune responses is predominantly induced depending on the antigen, the site of administration, and the type of the administration method. Administration may induce both of the Th1 and Th2 immune responses. The Th1 immune response can be effectively induced by the antigen-adjuvant microparticle complex having a small particle size, or the particle formed by association of the complexes, as shown in Examples. The degrees of the Th1 immune response and the Th2 immune response can be evaluated by various known methods. For example, in the case of mouse, the amount of production of the IgG2a antibody is known to be an index for the Th1 immune response. Further, as indices for the Th2 immune response, the IgG1 antibody and the total IgG antibody amount are known.

The immunogenic composition contains as an effective ingredient the antigen-adjuvant microparticle complex or the particle formed by association of the complex, and hence has an adjuvant capacity, but, by further inclusion of an immune-activating substance, a higher immune-activating capacity can be realized. The immune-activating substance may be either contained in the outside of the adjuvant microparticle or encapsulated therein, and the substance is preferably encapsulated in the adjuvant microparticle. The immune-activating substance is not restricted as long as it may function as an immune-activating substance, and examples thereof include oils, aluminum salts, calcium salts, gel-forming polymers, immune-activating cytokines and TLR receptor ligands, among which immune-activating cytokines and TLR receptor ligands are preferred.

Examples of the immune-activating cytokines include interleukin 12, interferon α, interleukin 18, TNFα, interleukin 6, NO, interferon γ and interferon β.

Examples of the TLR receptor ligands include lipoproteins; double-stranded RNAs such as poly I:C and poly I:CLC; flagellin; single-stranded RNAs; CpG; profilin; MPL; QS21; and TDM, among which nucleic acids such as double-stranded RNAs, single-stranded RNAs and CpG are preferred, and CpG is more preferred. The CpG herein means unmethylated CpG (cytosine-guanine)-motif DNAs existing in viruses, bacteria and the like (see Japanese Translated PCT Patent Application Laid-open No. 2001-503254). Various effective sequences are reported as CpG motifs, and the type of the sequence is not restricted as long as it has an immune-activating capacity, and the sequence may be prepared using a base analogue or may be selected from various types of modified products.

In cases where the immunogenic composition is used as a pharmaceutical composition or a vaccine, various pharmaceutically useful additives may be contained in addition to the amphiphilic polymer, hydrophilic active substance, surface modifier and disperse medium. Examples of the additives which may be added include buffers, antioxidants, salts, polymer and sugars.

The method of induction of an immune response using the immunogenic composition is not restricted, and the immunogenic composition may be either administered to a living body or brought into contact with immunocompetent cells removed to the outside of a living body. The method of administration of the immunogenic composition to a living body is not restricted, and examples thereof include subcutaneous administration, intradermal administration, intramuscular administration, transnasal administration, pulmonary administration, oral administration, sublingual administration, intravaginal administration, intraperitoneal administration and lymph node administration, among which intradermal administration and subcutaneous administration are preferred.

In terms of the amount of the immunogenic composition to be used upon induction of the immune response, the necessary amount of the antigen required for induction of the immune reaction of interest is set appropriately depending on the type of the antigen, administration method, and number of doses. For example, in cases where the immunogenic composition is subcutaneously administered to human to induce the immune response, 0.01 to 1,000 μg per dose of the antigen is administered, which antigen is contained in the immunogenic composition. The number of doses may also be appropriately set similarly to the dose, and the immune response can be induced by 1 to 10 times of administration since the immunogenic composition has an action to induce an immune response continuously.

The living body to which the immunogenic composition is administered may be either human or a non-human animal, and the living body is preferably human; or pig, cow, bird, sheep, horse, donkey, goat or camel, dog, cat, ferret, rabbit, monkey, rat, mouse or guinea pig, which is kept as a livestock, pet animal or experimental animal.

EXAMPLES

Examples are described below, but this disclosure is not restricted to these Examples.

Example 1

Synthesis of Dextran-Poly(lactic-co-glycolic acid) (PLGA)

(1-1) Synthesis of TMS-Dextran

Dextran (Nacalai Tesque; special grade according to Nacalai standards; number average molecular weight, 13,000; 5.0 g) was added to formamide (100 ml), and the resulting mixture was heated to 80° C. To this solution, 1,1,1,3,3,3-hexamethyldisilazane (100 ml) was added dropwise for 20 minutes. Thereafter, the resulting mixture was stirred at 80° C. for 2 hours. After completion of the reaction, the reaction solution was allowed to cool to room temperature, and two layers were separated from each other with a separatory funnel. The upper layer was concentrated under reduced pressure, and methanol (300 ml) was added thereto, followed by filtering and drying the obtained solids, to obtain TMS-dextran (Compound (1)) (11.4 g) as white solids.

By the same method, Compounds (2) and (3) were prepared using dextran (manufactured by Sigma; average molecular weight, not more than 1,500); Compounds (4) and (5) were prepared using dextran (manufactured by SERVA; average molecular weight, not more than 5,000); Compound (6) was prepared using dextran (the same reagent as the one used for the preparation of Compound (1)); and Compounds (7), (8) and (9) were prepared using dextran (manufactured by Nacalai Tesque; average molecular weight, 40,000).

(1-2) Synthesis of Dextran-PLGA (Compounds (12)-(23))

Compound (1) (0.5 g) and potassium tert-butoxide (35 mg) were dried under heat under reduced pressure for 2 hours, and tetrahydrofuran (10 ml) was added thereto, followed by stirring the resulting mixture for 1.5 hours at room temperature. To this solution, a solution of (DL)-lactide (0.56 g) and glycolide (0.45 g) in tetrahydrofuran (15 ml) was added dropwise, and the resulting mixture was stirred for 5 minutes, followed by adding 2 drops of acetic acid to stop the reaction. After completion of the reaction, the solvent was concentrated under reduced pressure, and reprecipitation purification with the chloroform-methanol system and the chloroform-diethyl ether system was carried out, to obtain white solids, which were then dissolved in chloroform (9 ml). To the resulting solution, trifluoroacetic acid (1.0 ml) was added, and the resulting mixture was stirred at room temperature for 30 minutes. After completion of the reaction, the solvent was evaporated under reduced pressure, and the residue was dissolved in chloroform (10 ml), followed by adding the resulting solution to diethyl ether which had been preliminarily cooled to 0° C. and filtering the obtained product, to obtain dextran-PLGA as white solids (Compound (12)). By the same method, Compound (13) was synthesized with (DL)-lactide (0.78 g) and glycolide (0.63 g); Compound (14) was synthesized with (DL)-lactide (1.12 g) and glycolide (0.9 g); Compound (15) was synthesized with (DL)-lactide (1.67 g) and glycolide (1.35 g).

Further, Compound (16) was synthesized using Compound (2) with (DL)-lactide (0.56 g) and glycolide (0.45 g); Compound (17) was synthesized using Compound (3) with (DL)-lactide (0.67 g) and glycolide (0.54 g); Compound (18) was synthesized using Compound (4) with (DL)-lactide (0.78 g) and glycolide (0.63 g); Compound (19) was synthesized using Compound (5) with (DL)-lactide (0.89 g) and glycolide (0.72 g); Compound (20) was synthesized using Compound (6) with (DL)-lactide (0.78 g) and glycolide (0.63 g); Compound (21) was synthesized using Compound (7) with (DL)-lactide (0.78 g) and glycolide (0.63 g); Compound (22) was synthesized using Compound (8) with (DL)-lactide (1.12 g) and glycolide (0.9 g); and Compound (23) was synthesized using Compound (9) with (DL)-lactide (1.12 g) and glycolide (0.9 g).

The weight average molecular weight and the number average molecular weight of each of the polymers of Compounds (12) to (15) were determined by GPC measurement (column: manufactured by Tosoh Corporation, TSK-gel α-5000×2, DMF solvent; detector: RI; standard: pullulan). The number average molecular weight and the number of graft chains of Compounds (12) to (23) were determined by $^1$H-NMR measurement (Table 1).

TABLE 1

Evaluation results of Dex-g-PLGA polymers prepared

| Compound ID | Weight average molecular weight | Number average molecular weight | Molecular weight of graft chain | Number of graft chains | TMS-Dex Compound ID |
|---|---|---|---|---|---|
| (12) | 99462 | 85101 | 2167 | 31-41 | (1) |
| (13) | 116570 | 101126 | 3000 | 23-31 | (1) |
| (14) | 144878 | 122151 | 4864 | 20-22 | (1) |
| (15) | 172500 | 154008 | 5792 | 18-24 | (1) |
| (16) | — | — | 2786 | 2 | (2) |
| (17) | — | — | 4070 | 2.2 | (3) |
| (18) | — | — | 3120 | 8.3 | (4) |
| (19) | — | — | 4275 | 10.9 | (5) |
| (20) | — | — | 3250 | 17 | (6) |
| (21) | — | — | 4333 | 41 | (7) |
| (22) | — | — | 5571 | 15 | (8) |
| (23) | — | — | 4333 | 21 | (9) |

Example 2

Synthesis of PEG-PLGA (Compounds (10), (11))

Polyethylene glycol monomethyl ether (NIPPON OIL & FATS CO., LTD.; SUNBRIGHT MEH-20H; number average molecular weight, 5,128; Mw/Mn=1.02), (DL)-lactide and glycolide were mixed together in the feeding amounts shown in Table 2, and the resulting mixture was heated to 140° C. After stirring the mixture for 20 minutes, tin octylate (II) (0.05 wt % with respect to polyethylene glycol monomethyl ether) was added to the mixture, and the resulting mixture was stirred at 180° C. for 3 hours. The reaction liquid was allowed to cool to room temperature, and dissolved in chloroform (such that the concentration becomes about 100 mg/ml), followed by reprecipitation purification with diethyl ether which had been preliminarily cooled to 0° C. The obtained solids were filtered, and dried under reduced pressure, to obtain a PEG-PLGA polymer as white or light-brown solids. The number average molecular weight of the polymer was determined by $^1$H-NMR (Table 2).

TABLE 2

Evaluation results of PEG-PLGA polymers prepared

| Compound ID | Fed amount of PEG | Fed amount of DL-lactide | Fed amount of glycolide | Number average molecular weight |
|---|---|---|---|---|
| (10) | 300 mg | 2.16 g | 1.74 g | 60000 |
| (11) | 100 mg | 1.15 g | 0.93 g | 110000 |

Example 3

Preparation of Antigen-Adjuvant Microparticle Complexes Using Dex-g-PLGA Polymers (Dex-g-PLGA Particles (1)-(28))

In 100 μl of dimethyl carbonate, 5 mg of dextran-poly (lactic-co-glycolic acid) (PLGA) (Compounds (12)-(23)) in Example 1 was dissolved, to prepare a 50 mg/ml polymer solution. To this polymer solution, 20 μl of tert-butanol was added, and 50 μl of the encapsulated antigen ((OVA (ovalbumin) (Sigma) or CEA (carcinoembryonic antigen) (COSMO BIO Co., Ltd.)) and/or immune-activating substance (CpG) shown in Table 3 was/were added to the concentration(s) described, and the resulting mixture was stirred with a vortex mixer, to produce a reversed-phase emulsion. As the Cpg, 5'-gggggggCGACGATCGTCAgG-3' (lowercase letters represent phosphorothioate-modified bases) (contract synthesis by Sigma-Genosys) was used.

The reversed-phase emulsion was subjected to prior freezing with liquid nitrogen, and freeze-dried using a freeze dryer (EYELA, FREEZE DRYER FD-1000) at a trap cooling temperature of −45° C. at a degree of vacuum of 20 Pa for 24 hours. The obtained solids were dispersed in the dispersion medium in the amount shown in Table 3, to prepare an S/O suspension. The S/O suspension was added dropwise to 2 ml of an aqueous 10% Pluronic F-68-containing solution, and the resulting mixture was stirred/emulsified by the stirring method described in Table 3, to prepare an S/O/W emulsion. From the S/O/W emulsion, the water-immiscible organic solvent was removed by solvent evaporation, to provide an antigen-adjuvant microparticle complex dispersion. The dispersion was subjected to prior freezing with liquid nitrogen, and freeze-dried using a freeze dryer (EYELA, FREEZE DRYER FD-1000) at a trap cooling temperature of −45° C. at a degree of vacuum of 20 Pa for 24 hours, to obtain dry powder of an antigen-adjuvant microparticle complex (average particle size, 0.4 μm) and a particle (average particle size, 5 to 40 μm) formed by association of the antigen-adjuvant microparticle complex. The result of calculation of the average particle size of the obtained particle by observation with a scanning electron microscope (SEM: S-4800 manufactured by Hitachi, Ltd.) is shown in Table 3.

TABLE 3

Recipes and average particle sizes of Dex-g-PLGA particles

| Particle ID | Polymer used | Composition of solution in particle | Dispersion solution/ solution volume | Stirring method | Average particle size (μm) |
|---|---|---|---|---|---|
| (1) | Compound (12) | OVA (5 mg/ml) | Ethyl acetate 200 μl | Vortex mixer | 5 (Associated particle) |
| (2) | Compound (13) | OVA (5 mg/ml) | Ethyl acetate 200 μl | Vortex mixer | 5 (Associated particle) |
| (3) | Compound (14) | OVA (5 mg/ml) | Ethyl acetate 200 μl | Vortex mixer | 5 (Associated particle) |
| (4) | Compound (15) | OVA (5 mg/ml) | Ethyl acetate 200 μl | Vortex mixer | 5 (Associated particle) |
| (5) | Compound (14) | OVA (5 mg/ml) | Ethyl acetate 200 μl | Stirrer (1000 rpm) | 40 (Associated particle) |
| (6) | Compound (14) | OVA (5 mg/ml) | Ethyl acetate 500 μl | Vortex mixer | 0.4 |
| (7) | Compound (12) | CEA (0.5 mg/ml) | Ethyl acetate 200 μl | Vortex mixer | 5 (Associated particle) |
| (8) | Compound (13) | CEA (0.5 mg/ml) | Ethyl acetate 200 μl | Vortex mixer | 5 (Associated particle) |
| (9) | Compound (14) | CEA (0.5 mg/ml) | Ethyl acetate 200 μl | Vortex mixer | 5 (Associated particle) |
| (10) | Compound (15) | CEA (0.5 mg/ml) | Ethyl acetate 200 μl | Vortex mixer | 5 (Associated particle) |
| (11) | Compound (14) | CEA (0.5 mg/ml) | Ethyl acetate 200 μl | Stirrer (1000 rpm) | 40 (Associated particle) |
| (12) | Compound (14) | CEA (0.5 mg/ml) | Ethyl acetate 500 μl | Vortex mixer | 0.4 |
| (13) | Compound (14) | CEA (0.5 mg/ml) + CpG (2.5 mg/ml) | Ethyl acetate 200 μl | Vortex mixer | 5 (Associated particle) |
| (14) | Compound (16) | CEA (0.25 mg/ml) | Dimethyl carbonate 200 μl | Vortex mixer | 5 (Associated particle) |
| (15) | Compound (17) | CEA (0.25 mg/ml) | Dimethyl carbonate 200 μl | Vortex mixer | 5 (Associated particle) |
| (16) | Compound (18) | CEA (0.25 mg/ml) | Dimethyl carbonate 200 μl | Vortex mixer | 5 (Associated particle) |
| (17) | Compound (19) | CEA (0.25 mg/ml) | Dimethyl carbonate 200 μl | Vortex mixer | 5 (Associated particle) |
| (18) | Compound (20) | CEA (0.25 mg/ml) | Dimethyl carbonate 200 μl | Vortex mixer | 5 (Associated particle) |
| (19) | Compound (21) | CEA (0.25 mg/ml) | Dimethyl carbonate 200 μl | Vortex mixer | 5 (Associated particle) |
| (20) | Compound (22) | CEA (0.25 mg/ml) | Dimethyl carbonate 200 μl | Vortex mixer | 0.4 |
| (21) | Compound (22) | CEA (0.25 mg/ml) | Dimethyl carbonate 200 μl | Vortex mixer | 5 (Associated particle) |
| (22) | Compound (22) | CEA (0.25 mg/ml) | Dimethyl carbonate 200 μl | Stirrer (1000 rpm) | 40 (Associated particle) |
| (23) | Compound (23) | OVA (5 mg/ml) | Dimethyl carbonate 200 μl | Vortex mixer | 5 (Associated particle) |
| (24) | Compound (23) | None | Dimethyl carbonate 200 μl | Vortex mixer | 5 (Associated particle) |
| (25) | Compound (23) | CEA (0.25 mg/ml) | Ethyl acetate 200 μl | Vortex mixer | 0.4 |
| (26) | Compound (23) | CEA (0.25 mg/ml) | Ethyl acetate 200 μl | Vortex mixer | 5 (Associated particle) |
| (27) | Compound (23) | CEA (0.25 mg/ml) | Ethyl acetate 200 μl | Stirrer (1000 rpm) | 40 (Associated particle) |
| (28) | Compound (23) | CEA (0.025 mg/ml) | Ethyl acetate 200 μl | Vortex mixer | 0.4 |

Example 4

Preparation of Antigen-Adjuvant Microparticle Complexes Using Peg-PLGA Polymers (PEG-PLGA particles (1) to (4))

In 100 μl of dimethyl carbonate, 5 mg of the PEG-PLGA polymer prepared in Example 2 (Compound (10) or (11)) was dissolved, to prepare a 50 mg/ml polymer solution. To this polymer solution, 20 μl of tert-butanol was added, and 50 μl of the antigen-containing solution shown in Table 4 was added to the resulting mixture, followed by stirring the mixture, to produce a reversed-phase emulsion solution. The reversed-phase emulsion solution was subjected to prior freezing with liquid nitrogen, and freeze-dried using a freeze dryer (EYELA, FREEZE DRYER FD-1000) at a trap cooling temperature of −45° C. at a degree of vacuum of 20 Pa for 24 hours. The obtained solids were dispersed in ethyl acetate in the amount shown in Table 4, to prepare an S/O suspension. The S/O suspension was added dropwise to 2 ml of an aqueous 10% Pluronic F-68-containing solution, and the resulting mixture was stirred/emulsified with a vortex mixer, to prepare an S/O/W emulsion. From the S/O/W emulsion, the water-immiscible organic solvent was removed by solvent evaporation, to provide an antigen-adjuvant microparticle complex dispersion. The dispersion was subjected to prior freezing with liquid nitrogen, and freeze-dried using a freeze dryer (EYELA, FREEZE DRYER FD-1000) at a trap cooling temperature of −45° C. at a degree of vacuum of 20 Pa for 24 hours, to obtain dry powder of an antigen-adjuvant microparticle complex. The result of calculation of the average particle size of the antigen-adjuvant microparticle complex by observation with a scanning electron microscope (SEM: S-4800 manufactured by Hitachi, Ltd.) is shown in Table 4.

dryer (EYELA, FREEZE DRYER FD-1000) at a trap cooling temperature of −45° C. at a degree of vacuum of 20 Pa for 12 hours, to obtain a PLGA particle containing an antigen. The obtained particle was observed with a scanning electron microscope (SEM: S-4800 manufactured by Hitachi, Ltd.) to calculate the average particle size, and the average particle size was revealed to be 2 μm. Further, the PLGA particle (2) was prepared using an aqueous CEA solution (0.25 mg/ml) and the average particle size was calculated in the same manner with SEM. The average particle size was revealed to be 2 μm.

Example 5

Measurement of Antigen Encapsulation Rates and Antigen Retention Capacities of CEA-Adjuvant Microparticle Complexes and Associated Particles Thereof Method In a 1.5-ml Eppendorf tube, 20 mg of each of the adjuvant microparticle complexes and their associated particles (hereinafter referred to as CEA-encapsulating particles) prepared by the methods of Examples 3 and 4 was placed, and dissolved in 1 ml of buffer A (PBS supplemented with 0.1% bovine serum albumin, 0.1% Pluronic F-68 and 0.02% sodium azide), followed by separation into particles (precipitate) and the supernatant by centrifugation at 18,000×g for 10 minutes. The supernatant was collected in another tube, and the particles were resuspended in 1 ml of a buffer, followed by carrying out the separation again into particles and the supernatant by centrifugation under the above conditions. This washing operation was repeated once more (a total of three times of centrifugation), and the CEA concentration of the

TABLE 4

Recipes and average particle sizes of PEG-PLGA particles

| Particle ID | Polymer used | Composition of solution in particle | Amount of ethyl acetate solution (μl) | Stirring method | Average particle size (μm) |
|---|---|---|---|---|---|
| (1) | Compound (10) | OVA (5 mg/ml) | 200 | Vortex mixer | 5 (Associated particle) |
| (2) | Compound (11) | OVA (5 mg/ml) | 200 | Vortex mixer | 5 (Associated particle) |
| (3) | Compound (10) | OVA (5 mg/ml) | 200 | Vortex mixer | 5 (Associated particle) |
| (4) | Compound (10) | CEA (5 mg/ml) | 200 | Vortex mixer | 5 (Associated particle) |

Comparative Example 1

Preparation of PLGA Homopolymer Particles Containing Antigen (PLGA Particles (1) and (2))

PLGA particles containing an antigen were prepared using a known technology (International Journal of Pharmaceutics, 2007, vol. 334, pp. 137-148). In 15 ml of methylene chloride, 200 mg of PLGA (manufactured by SIGMA; average molecular weight, 40,000-75,000) was dissolved, to prepare 13.3 mg/ml PLGA solution. To 2 ml of the polymer solution, 100 μl of 5 mg/ml aqueous OVA solution was added with stirring at 19,000 rpm (with a homogenizer manufactured by Polytron), and the stirring was further carried out in the same manner for 5 minutes, to produce a W/O solution. The W/O solution was added to 20 ml of 1% aqueous polyvinyl alcohol solution under stirring at 19,000 rpm, and the stirring was further carried out in the same manner for 5 minutes, to produce a W/O/W solution. The W/O/W solution was stirred at 200 rpm for 12 hours and then subjected to prior freezing with liquid nitrogen, followed by freeze-drying using a freeze supernatant collected by each time of centrifugation was measured using an ELISA kit (manufactured by Hope Laboratories, TM-201).

From the amount of CEA fed upon preparation of the particle (per a weight of the CEA-encapsulating particle of 20 mg), the total of the amounts of CEA in the supernatants obtained by the three times of centrifugation was subtracted, and the encapsulation rate was calculated according to the following equation:

$$\text{Encapsulation rate (\%)} = \text{Fed amount of CEA (ng)} - \text{Total CEA amount in supernatant (ng)} \times 100 \text{ Fed amount of CEA (ng)}. \quad \text{Equation 1}$$

In terms of measurement of the release capacity of the antigen, the particle after the three times of washing was suspended/dispersed in 1.2 ml of buffer A. A part of this liquid (40 μl) was transferred to another tube, and centrifugation was carried out at 18,000×g for 10 minutes to precipitate the particle, followed by collecting 30 μl of the supernatant in another tube (O-hour sample). The remaining particle suspension was gently mixed by inversion in a 1.5-ml Eppendorf tube placed in a 37° C. incubator using a rotator at a rate of 6 rpm. From this liquid, aliquots of a small amount (40 μl) were collected with time, and the supernatant was separated by centrifugation in the same manner as described above. The CEA concentration in the supernatant sample collected at each time point was measured by the above-described ELISA method, and the release rate (%) was calculated according to the following equation:

Release rate (%)=CEA concentration in supernatant (ng/ml)×1.2 (ml)×100 Amount of CEA encapsulated in 20 mg of CEA particle (ng).  Equation 2

Results

The antigen encapsulation rates of the CEA-encapsulating particles were as shown in Table 5, and it was revealed that the antigen was encapsulated in any of the CEA-encapsulating particles at a high rate. The retention capacity for the antigen was low in the Dex-g-PLGA particle (7) having short hydrophobic graft chains, wherein 67.3% of the encapsulated antigen was released in one week. On the other hand, as the length of the hydrophobic graft chain increased, the retention capacity for the antigen increased. In Dex-g-PLGA particles having long hydrophobic graft chains, about 90% of the fed antigen was still encapsulated even after one week. Also in the PEG-PLGA particle, only about 4% of the antigen was released in one week, showing a high antigen retention capacity.

TABLE 5

Encapsulation rates and antigen retention capacities of CEA-encapsulating particles

| CEA-encapsulating particle | Encapsulation rate (%) | Antigen release (%) (1 week) | Antigen release (%) (2 weeks) |
|---|---|---|---|
| Dex-g-PLGA particle (7) | 90.71 | 67.3 | 65.8 |
| Dex-g-PLGA particle (8) | 91.94 | 37.9 | 53.8 |
| Dex-g-PLGA particle (9) | 88.24 | 4.1 | 18.3 |
| Dex-g-PLGA particle (10) | 91.26 | 1.7 | 2.8 |
| Dex-g-PLGA particle (11) | 93.5 | 6.3 | 12.0 |
| Dex-g-PLGA particle (12) | 95 | 2.0 | 11.3 |
| PEG-PLGA particle (4) | 92.62 | 6.8 | 7.3 |
| Dex-g-PLGA particle (13) | 98.17 | 4.1 | 3.9 |

Example 6

Subcutaneous Administration of OVA-Containing Immunogenic Composition to Mice (1)

Method

Among the OVA-adjuvant microparticle complex-associated particles (hereinafter referred to as OVA-encapsulating associated particles) and OVA-adjuvant microparticle complexes (hereinafter referred to as OVA-encapsulating particles) prepared in Examples 3 and 4, 40 mg (50 μg in terms of the fed amount of antigen) each of OVA-encapsulating associated particles having hydrophobic chains having different lengths (Dex-g-PLGA particles (2), (3) and (4));

an OVA-encapsulating associated particle and an OVA-encapsulating particle having particle sizes different from that of the Dex-g-PLGA particle (3) (Dex-g-PLGA particles (5) and (6)); and a PEG-PLGA particle (3);

was suspended/dispersed in 3 ml of phosphate buffered saline (PBS), followed by centrifugation at 80×g for 5 minutes to precipitate the particle and transferring the supernatant to another tube. The supernatant was centrifuged again at 80×g for 5 minutes to precipitate the remaining particle, and the resulting supernatant was removed. The precipitates obtained in the first centrifugation and the second centrifugation were combined and redispersed in 1 ml of PBS, followed by repeating 3 times of the same centrifugation operation, thereby removing the antigen that was not encapsulated in the particle. The precipitate was finally redispersed in 150 μl of PBS, to provide a liquid for administration. This liquid was subcutaneously administered by single injection to the back of male Balb/C mice (Japan SLC, Inc.) of 9 weeks old. Administration, by single injection, of the PLGA particle produced in Comparative Example 1 or the antigen solution (50 μl) alone, as a Comparative Example; or a solution prepared by mixing 50 μl of the antigen solution with 50 μl of the adjuvant "Imject Alum" (manufactured by Thermo Scientific, hereinafter also referred to as Alum), as a Reference Example; was carried out. Under each condition, the administration was carried out for 4 individuals of mice, and the average values of the antibody titers are shown in FIG. 1.

The mice after administration were kept in an environment in which the mice can freely take food and water, while collecting blood from the tail vein with time. To the collected blood, heparin was added to a final concentration of 3.3 IU/ml, and centrifugation was carried out at 5,000 rpm for 5 minutes to collect blood plasma, followed by measuring the antibody titer against OVA in the blood plasma.

The antibody titer was measured by the following method. In a 96-well microplate (MaxiSorp, manufactured by Nunc), 100 μl of a PBS solution containing 1 μg/ml OVA was placed, and the plate was left to stand at 4° C. overnight. The solution was discarded, and 400 μl of PBS supplemented with 0.5% BSA was placed in the plate, followed by carrying out blocking at room temperature for 2 hours. The wells were washed once with 400 μl of a washing liquid (PBS supplemented with 0.05% Tween 20), and 100 μl of a blood plasma sample which had been 1,000- to 100,000-fold diluted with a dilution liquid (PBS supplemented with 0.25% BSA and 0.05% Tween 20) was placed in each well, followed by allowing the reaction to proceed at room temperature for 40 minutes with shaking. The wells were washed three times with the washing liquid, and 100 μl of HRP (horse radish peroxidase)-labeled anti-mouse IgG antibody (Zymed) (10,000-fold diluted with the dilution liquid) was placed in each well, followed by allowing the reaction to proceed at room temperature for 20 minutes with shaking. The wells were washed three times with the washing liquid, and 100 μl of a coloring liquid (0.1 M sodium acetate/citrate buffer (pH 4.5) containing 0.006% hydrogen peroxide and 0.2 mg/ml tetramethylbenzidine) was placed in each well, followed by allowing the reaction to proceed at room temperature for 10 minutes with shaking. The reaction was stopped by addition of 100 μl of 1 N sulfuric acid, and the absorbance at 450 nm was measured using a microplate reader. As a standard sample, a serially diluted anti-OVA monoclonal antibody (HYB 094-05, manufactured by Antibody Shop) was measured at the same time to provide a calibration curve, and the amount of the antibody in each sample was calculated as a concentration by weight (ng/ml).

Results

Change in the average value of the anti-OVA antibody titer in blood plasma with time is shown in FIG. 1. The OVA-encapsulating particle and the OVA-encapsulating associated particles using Dex-g-PLGA (Dex-g-PLGA particles (2), (3), (4), (5) and (6)), and the OVA-encapsulating associated particle using PEG-PLGA (PEG-PLGA particle (3)) showed continuous antibody titer-increasing effect for not less than 6 weeks, showing much higher values than the cases of administration of the PLGA particle or the antigen alone in the Comparative Examples and the case of administration of the antigen+Alum in the Reference Example. The Dex-g-PLGA particle (6), which has a small particle size, showed a tendency to have the highest antibody titer-increasing effect.

Example 7

Subcutaneous Administration of CEA-Containing Immunogenic Composition to Mice

Method

Figure 2:
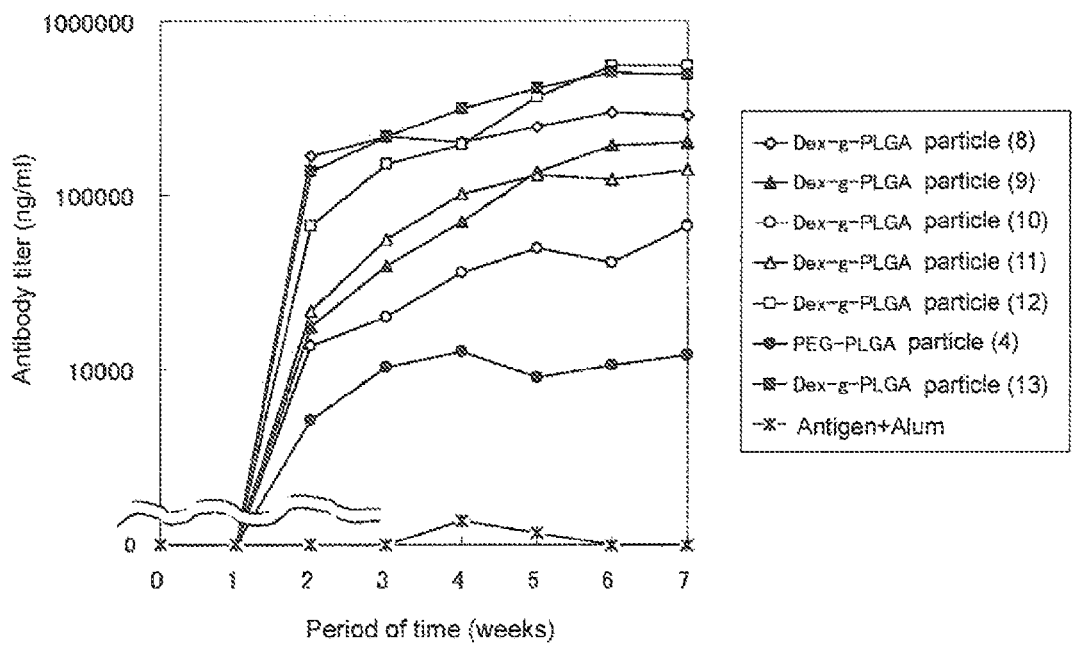
FIG. 2 shows immunological evaluation (total IgG) of CEA-containing immunogenic compositions.
Figure 3:
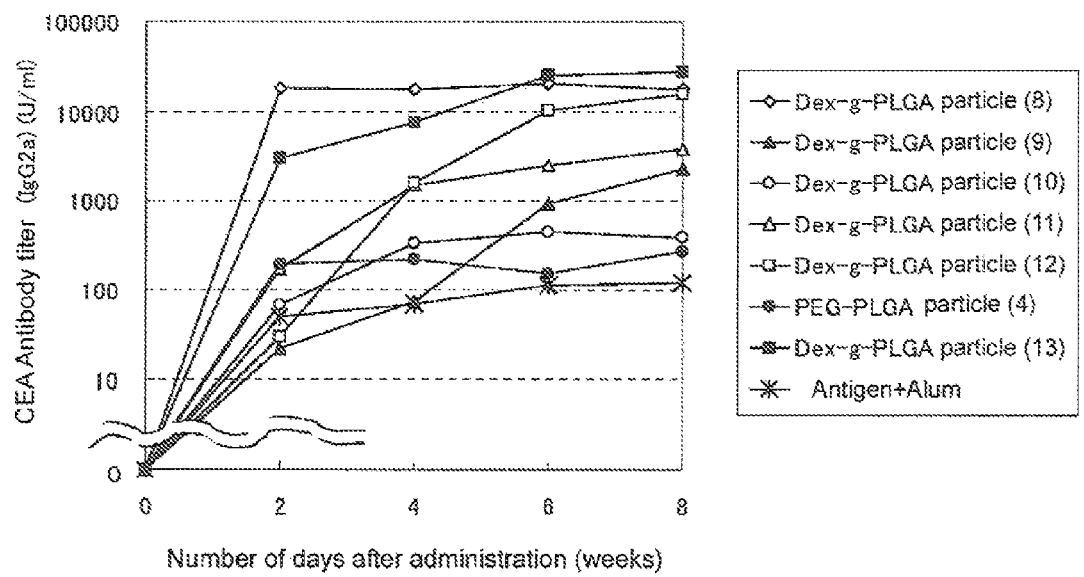
FIG. 3 shows immunological evaluation (IgG2a) of CEA-containing immunogenic compositions.

The CEA-adjuvant microparticle complexes (hereinafter referred to as CEA-encapsulating particles) and associated particles thereof (hereinafter referred to as CEA-encapsulating associated particles) prepared by the methods of Examples 3 and 4 were evaluated by the same method as in Example 6. The dose per individual was 1 mg (5 μg in terms of the antigen), and this dose was administered by single injection. As the CEA-encapsulating particles and the CEA-encapsulating associated particles, the Dex-g-PLGA particles (8), (9) and (10), which have hydrophobic graft chains having different lengths; the Dex-g-PLGA particles (11) and (12), which were prepared using Compound (4) as in the case of the Dex-g-PLGA particle (9) and have different particle sizes; the Dex-g-PLGA particle (13), which was prepared by incorporating the antigen and 25 μg of CpG into the Dex-g-PLGA particle (9); and the PEG-PLGA particle (4); were evaluated. Further, 50 μl of an aqueous solution containing 5 μg of the antigen, as a Comparative Example; and a mixture of 50 μl of an aqueous solution containing 5 μg of the antigen and 50 μl of Alum, as a Reference Example; were administered by single injection. Under each condition, the administration was carried out for 4 individuals of mice, and the average values for the respective groups are shown in FIG. 2 and FIG. 3.

The antibody titer against CEA was measured by the following method. In a 96-well microplate (MaxiSorp, manufactured by Nunc), 100 μl of a PBS solution containing 1 μg/ml CEA protein was placed, and the plate was left to stand at 4° C. overnight. The solution was discarded, and 400 μl of PBS supplemented with 0.5% BSA was placed in the plate, followed by carrying out blocking at room temperature for 2 hours. The wells were washed once with 400 μl of a washing liquid (PBS supplemented with 0.05% Tween 20), and 100 μl of a blood plasma sample which had been 1,000- to 100,000-fold diluted with a dilution liquid (PBS supplemented with 0.25% BSA and 0.05% Tween 20) was placed in each well, followed by allowing the reaction to proceed at room temperature for 40 minutes with shaking. The wells were washed three times with the washing liquid, and 100 μl of HRP (horse radish peroxidase)-labeled anti-mouse IgG antibody (Zymed) (10,000-fold diluted with the dilution liquid) was placed in each well, followed by allowing the reaction to proceed at room temperature for 20 minutes with shaking. The wells were washed three times with the washing liquid, and 100 μl of a coloring liquid (0.1 M sodium acetate/citrate buffer (pH 4.5) containing 0.006% hydrogen peroxide and 0.2 mg/ml tetramethylbenzidine) was placed in each well, followed by allowing the reaction to proceed at room temperature for 10 minutes with shaking. The reaction was stopped by addition of 100 μl of 1 N sulfuric acid, and the absorbance at 450 nm was measured using a microplate reader. As a standard sample, a serially diluted anti-CEA monoclonal antibody (MA1-5308, manufactured by Affinity Bioreagents) was measured at the same time to provide a calibration curve, and the amount of the antibody in each sample was calculated as a concentration by weight (ng/ml).

For measurement of the IgG2a antibody titer, an HRP-labeled anti-mouse IgG2a antibody (A90-107P, manufactured by Bethyl) was used instead of the HRP-labeled anti-mouse IgG antibody, and a blood plasma sample from a single individual of mouse whose antibody titer had increased was used as a reference sample. Samples prepared by serial dilution of this sample were used as a standard to prepare a calibration curve. The antibody titer corresponding to the 64,000-fold diluted sample was represented as 1 U.

Results

The CEA-encapsulating particles and the CEA-encapsulating associated particles using Dex-g-PLGA (the Dex-g-PLGA particles (8), (9), (10), (11) and (12), and the PEG-PLGA particle (4)) showed continuous increase in the antibody titer for about 6 weeks. Among these, the CEA-encapsulating particle having a small particle size (Dex-g-PLGA particle (12)) showed the highest antibody titer-increasing effect. Further, the Dex-g-PLGA particle (13) containing CpG together with the antigen showed a higher antibody titer-increasing effect than the Dex-g-PLGA particle (9) (FIG. 2).

Continuous increase in the anti-IgG2a antibody titer was confirmed for the Dex-g-PLGA particles (8), (9), (10), (11) and (12), and the PEG-PLGA particle (4). The Dex-g-PLGA particle (13) prepared by incorporating the antigen and CpG into the Dex-g-PLGA particle (9) showed a higher antibody titer-increasing effect than the Dex-g-PLGA particle (9). On the other hand, in the Reference Example wherein the mixture of the antigen and Alum was administered, continuous increase in the antibody titer was observed, but the effect was weaker than in the cases of the other Dex-g-PLGA particles. It was confirmed that the immunogenic composition of the present invention activated cell-mediated immunity, for which increase in the mouse IgG2a titer is known to be an index, continuously for a long time (FIG. 3).

Example 8

Subcutaneous Administration of OVA-Containing Immunogenic Composition to Mice (2)

Method

Using a Dex-g-PLGA polymer prepared by the same method as in the case of Compound (4) in Example 1, a particle prepared by the same method as in the case of the Dex-g-PLGA particle (3) in Example 3 (Dex-g-PLGA particle (A)) was evaluated by the method described in Example 6. The dose per individual was 16 mg (20 μg in terms of the amount of encapsulated OVA), and this dose was administered by single injection. Further, as a Reference Example, a solution prepared by mixing 50 μl of an aqueous solution containing 20 μg of the OVA antigen and 50 μl of Alum was administered by injection, once, or three times at intervals of 1 week. Under each condition, the administration was carried out for 2 individuals of mice, and the average values of the antibody titers are represented in FIG. 4 as measured values of the absorbance at 450 nm.

Results

Figure 4:
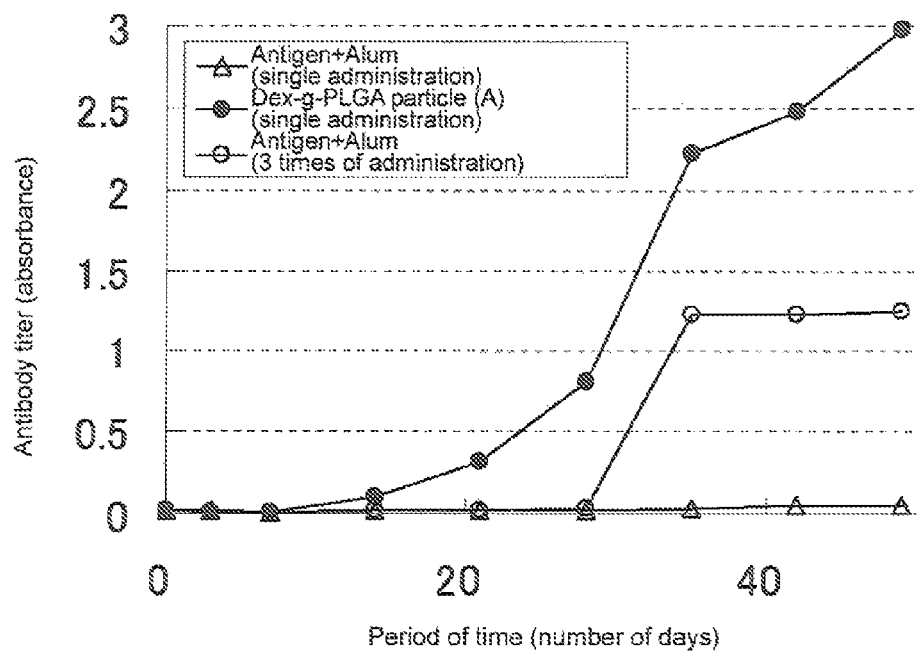
FIG. 4 shows immunological evaluation 2 of OVA-containing immunogenic compositions.

Change in the anti-OVA antibody in blood plasma with time is shown in FIG. 4. In the Reference Example in which the mixture of Alum and the antigen was administered once, increase in the antibody titer was hardly observed. In the Reference Example in which Alum and the antigen were administered three times, sharp increase in the antibody titer was observed after the third administration, but the increase was transient, and no increase was observed on Day 35 and later. In the mice to which the immunogenic composition of the present invention (Dex-g-PLGA particle (A)) was administered by single injection, continuous increase was observed from two weeks after the administration, and continuous increase in the antibody titer was confirmed until Day 56.

Example 9

Subcutaneous Administration of OVA-Containing Immunogenic Composition to Mice (3)

Method

Figure 5:
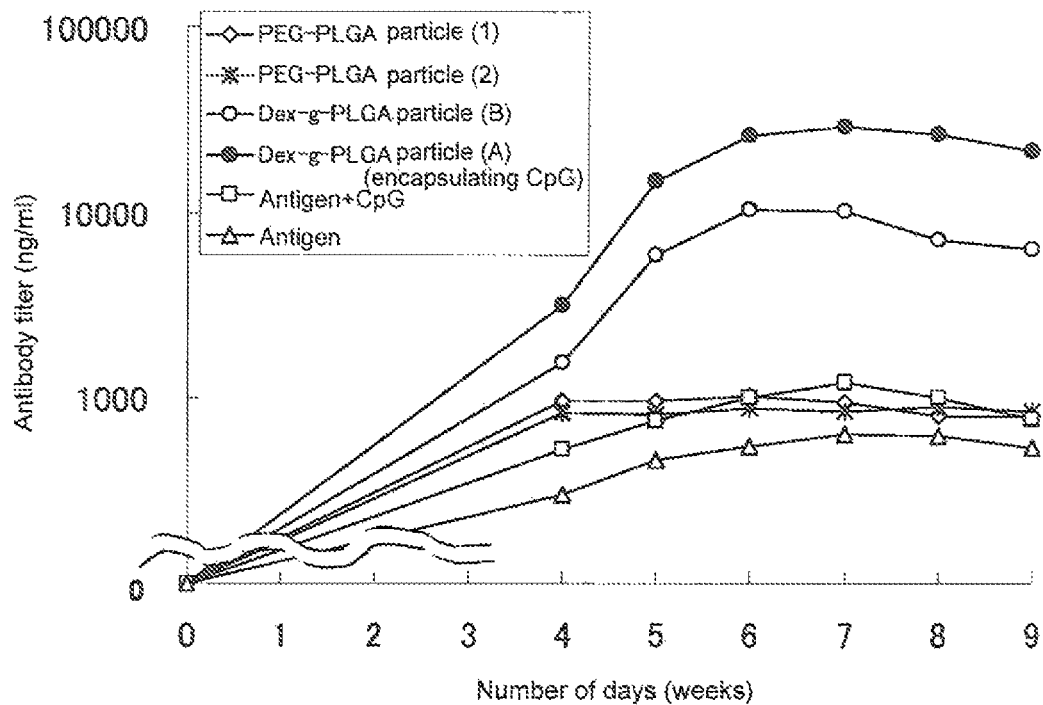
FIG. 5 shows immunological evaluation 3 of OVA-containing immunogenic compositions.

The evaluation was carried out by the same method as in Example 6. The dose of the OVA-encapsulating associated particle per individual was 10 mg (12.5 µg in terms of the fed amount of the antigen). A particle prepared using a Dex-g-PLGA polymer prepared by the same method as in the case of Compound (4) in Example 1, which particle was prepared by the same method as in the case of the Dex-g-PLGA particle (3) in Example 3 (Dex-g-PLGA particle (B)); a particle prepared using a Dex-g-PLGA polymer prepared by the same method as in the case of Compound (4) in Example 1, which particle was prepared by incorporation of CpG together with OVA during preparation of the Dex-g-PLGA particle (3) in Example 3 such that the dose of the CpG per individual is 6.25 µg (Dex-g-PLGA particle (C)); or the PEG-PLGA particle (1) or (2); was administered by single injection. As a Comparative Example, 12.5 µg of the antigen was administered, and, as a Reference Example, a mixture of 12.5 µg of the antigen and 6.25 µg of CpG was administered, by single injection. Blood was collected from 4 weeks after the administration at intervals of 1 week, and the antibody titer was measured by the same method as in Example 6. Under each condition, the administration was carried out for 2 individuals of mice, and the average values of the antibody titers are shown in FIG. 5.

Results

Any of the OVA-encapsulating associated particles (the PEG-PLGA particles (1) and (2), and the Dex-g-PLGA particles (B) and (C)) caused increase in the antibody titer of the animal to which the particle was administered, for not less than 6 weeks after the administration. The Dex-g-PLGA particles showed higher immune-activating capacities than the PEG-PLGA particles. Further, the OVA-encapsulating particle in which CpG is encapsulated (Dex-g-PLGA particle (C)) showed a higher antibody titer-increasing effect than the OVA-encapsulating particle which does not contain CpG (Dex-g-PLGA particle (B)).

Example 10

Subcutaneous Administration of HCV Structural Protein-Containing Immunogenic Composition to Mice Method Using a Dex-g-PLGA polymer prepared by the same method as in the case of Compound (4) in Example 1, and using the same preparation method as in the case of the Dex-g-PLGA particle (3) in Example 3, a Dex-g-PLGA particle (D) (hereinafter referred to as HCV-E2-encapsulating associated particle) was prepared, which Dex-g-PLGA particle (D) was formed by association of an HCV structural protein-adjuvant microparticle complex containing an HCV structural protein. This particle was administered by single injection by the same method as in Example 6. As the HCV structural protein, a chimeric protein composed of the E2 protein derived from the J6CF strain and the Fc protein of human IgG, which chimeric protein was prepared according to the method described in Japanese patent application No. 2008-254338, was used. The dose per individual was 80 mg (1.5 µg in terms of the antigen). Further, a mixture of 25 µg of CpG and the Dex-g-PLGA particle (D), and a mixture of 25 µg of CpG, 50 µl of Alum and the Dex-g-PLGA particle (D) were administered by single injection, respectively. As a Comparative Example, 1.5 µg of the antigen alone was administered, and, as Reference Examples, 100 µl of an aqueous solution containing 1.5 µg of the antigen and 25 µg of CpG, 100 µl of an aqueous solution containing 1.5 µg of the antigen and 50 µl of Alum, and 100 µl of an aqueous solution containing 1.5 µg of the antigen, 50 µl of Alum and 25 µg of CpG were administered by single injection, respectively. Under each condition, the administration was carried out for 2 individuals of mice.

Figure 6:
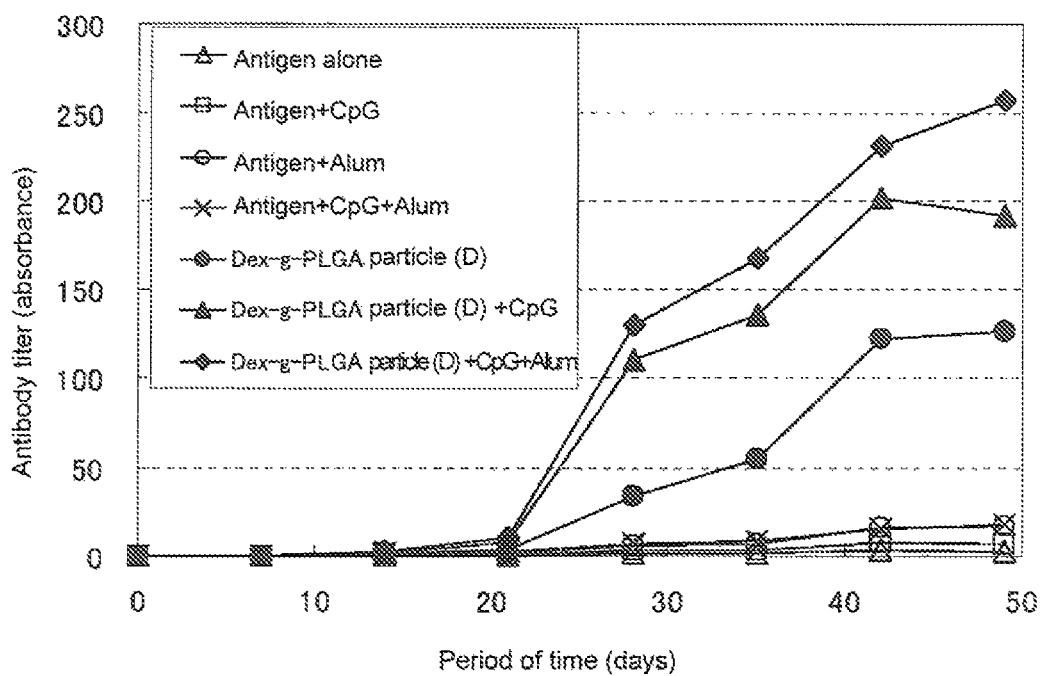
FIG. 6 shows immunological evaluation of HCV structural protein-containing immunogenic compositions.

The antibody titer against the HCV structural protein was measured by the following method. In a 96-well microplate (MaxiSorp, manufactured by Nunc), 100 µl of a PBS solution containing 0.5 µg/ml HCV structural protein was placed, and the plate was left to stand at 4° C. overnight. The solution was discarded, and 400 µl of PBS supplemented with 0.5% BSA was placed in each well, followed by carrying out blocking at room temperature for 2 hours. The wells were washed once with 400 µl of a washing liquid (PBS supplemented with 0.05% Tween 20), and 100 µl of a blood plasma sample which had been 1,000- to 100,000-fold diluted with a dilution liquid (PBS supplemented with 0.25% BSA and 0.05% Tween 20) was placed in each well, followed by allowing the reaction to proceed at room temperature for 40 minutes with shaking. The wells were washed three times with the washing liquid, and 100 µl of HRP (horse radish peroxidase)-labeled anti-mouse IgG antibody (Zymed) (10,000-fold diluted with the dilution liquid) was placed in each well, followed by allowing the reaction to proceed at room temperature for 20 minutes with shaking. The wells were washed three times with the washing liquid, and 100 µl of a coloring liquid (0.1 M sodium acetate/citrate buffer (pH 4.5) containing 0.006% hydrogen peroxide and 0.2 mg/ml tetramethylbenzidine) was placed in each well, followed by allowing the reaction to proceed at room temperature for 10 minutes with shaking. The reaction was stopped by addition of 100 µl of 1 N sulfuric acid, and the absorbance at 450 nm was measured using a microplate reader. In FIG. 6, the average values of the antibody titers are represented as measured values of the absorbance at 450 nm.

Results

The HCV-E2-encapsulating associated particle (Dex-g-PLGA particle (D)) showed continuous antibody titer-increasing effect for 7 weeks. Further, in the case where the HCV-E2-encapsulating associated particle was mixed with CpG, and in the case where the HCV-E2-encapsulating associated particle was mixed with CpG and Alum, a higher antibody titer-increasing effect was obtained compared to the case where the HCV-E2-encapsulating associated particle alone was administered. In the Comparative Example wherein the antigen alone was administered, increase in the antibody titer was hardly observed. In the Reference Examples wherein the mixture of the antigen and Alum; mixture of the antigen and CpG; or mixture of the antigen, CpG and Alum; was administered, the antibody titer-increasing effect was higher than in the case of administration of the antigen alone, but the titer-increasing effect was much lower than in the case of administration of the HCV-E2-encapsulating associated particle.

Example 11

Subcutaneous Administration of CEA-Containing Immunogenic Composition to Mice (2)

Method

Figure 7:
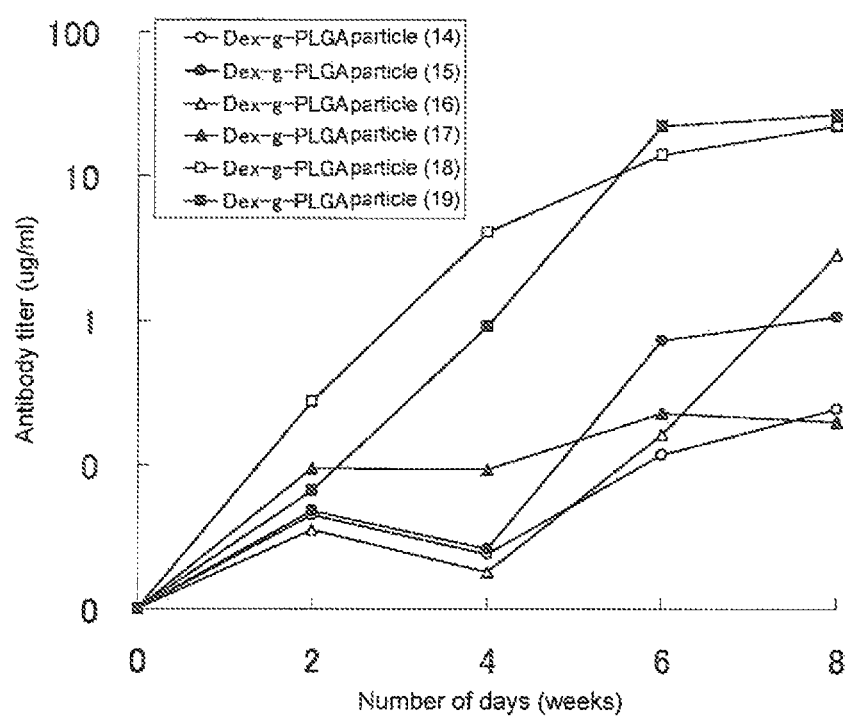
FIG. 7 shows immunological evaluation 2 of CEA-containing immunogenic compositions.

The CEA-adjuvant microparticle complex-associated particles prepared by the methods in Examples 3 and 4 (hereinafter referred to as CEA-encapsulating associated particles) were evaluated by the same method as in Example 7. The dose per individual was 400 µg (1 µg in terms of the antigen), and this dose was administered at Week 0 and Week 4. As the CEA-encapsulating associated particles, the Dex-g-PLGA particles (14) and (15) having hydrophilic chains of dextran having a molecular weight of 1,500, Dex-g-PLGA particles (16) and (17) having hydrophilic chains of dextran having a molecular weight of 5,000, Dex-g-PLGA particle (18) having hydrophilic chains of dextran having a molecular weight of 175,000, and Dex-g-PLGA particle (19) having hydrophilic chains of dextran having a molecular weight of 40,000 were evaluated. Under each condition, the administration was carried out for 5 individuals of mice, and the average value in each group is shown in FIG. 7. The antibody titer against CEA was measured by the same method as in Example 7.

Results

The CEA-encapsulating associated particles using Dex-g-PLGA (Dex-g-PLGA particles (14), (15), (16), (17), (18) and (19)) showed continuous increase in the antibody titer. Among these, the CEA-encapsulating associated particles constituted by dextran having a molecular weight of 175,000 and a molecular weight of 40,000 (Dex-g-PLGA particles (18) and (19)) showed higher antibody titer-increasing effects than the CEA-encapsulating associated particles constituted by dextran hydrophilic chains having a molecular weight of 1,500 and a molecular weight of 5,000 (Dex-g-PLGA particles (14), (15), (16) and (17)) (FIG. 7).

Example 12

Subcutaneous Administration of CEA-Containing Immunogenic Composition to Mice (3)

Method

Figure 8:
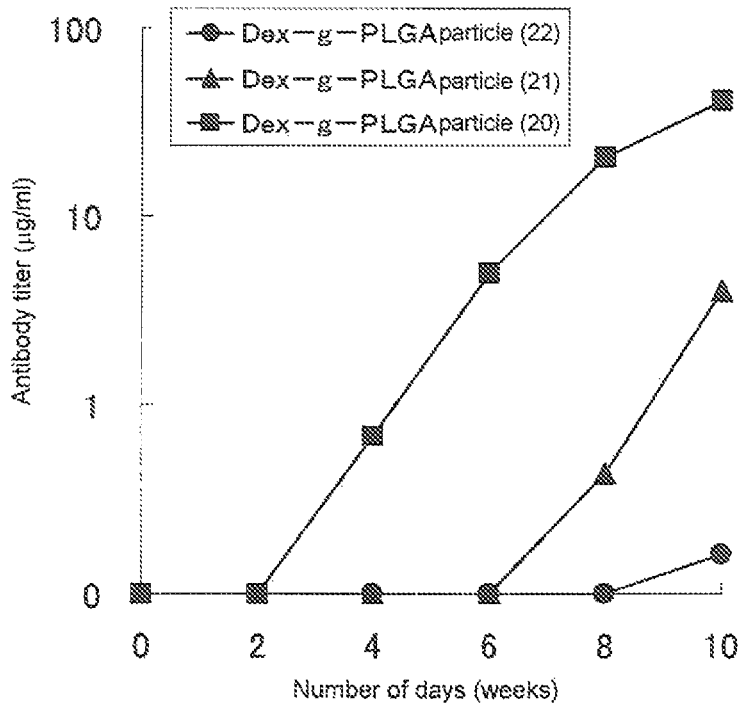
FIG. 8 shows immunological evaluation 3 of CEA-containing immunogenic compositions.

The CEA-adjuvant microparticle complex-associated particles (hereinafter referred to as CEA-encapsulating associated particles) prepared by the methods of Examples 3 and 4 were evaluated by the same method as in Example 7. The dose per individual was 400 µg (1 µg in terms of the antigen), and this dose was administered at Week 0 and Week 4. As the CEA-encapsulating associated particles, 3 types of particles which were prepared using the same polymer but have different particle sizes (Dex-g-PLGA particle (20) (particle size, 0.4 µm), Dex-g-PLGA particle (21) (particle size, 5 µm) and Dex-g-PLGA particle (particle size, 40 µm)) were evaluated. Under each condition, the administration was carried out for 5 individuals of mice, and the average value in each group is shown in FIG. 8. The antibody titer against CEA was measured by the same method as in Example 7.

Results

The CEA-encapsulating particle and CEA-encapsulating associated particles using Dex-g-PLGA (Dex-g-PLGA particles (20), (21) and (22)) showed continuous increase in the antibody titer. Among these, the Dex-g-PLGA particle (20) having an average particle size of 0.4 µm showed the highest antibody titer-increasing effect; the Dex-g-PLGA particle (21) having an average particle size of 5 µm showed the second highest antibody titer-increasing effect; and the Dex-g-PLGA particle (22) having an average particle size of 40 µm showed the lowest antibody titer-increasing effect (FIG. 8).

Example 13

Subcutaneous Administration of OVA-Containing Immunogenic Composition to Mice (4)

Method

Figure 9:
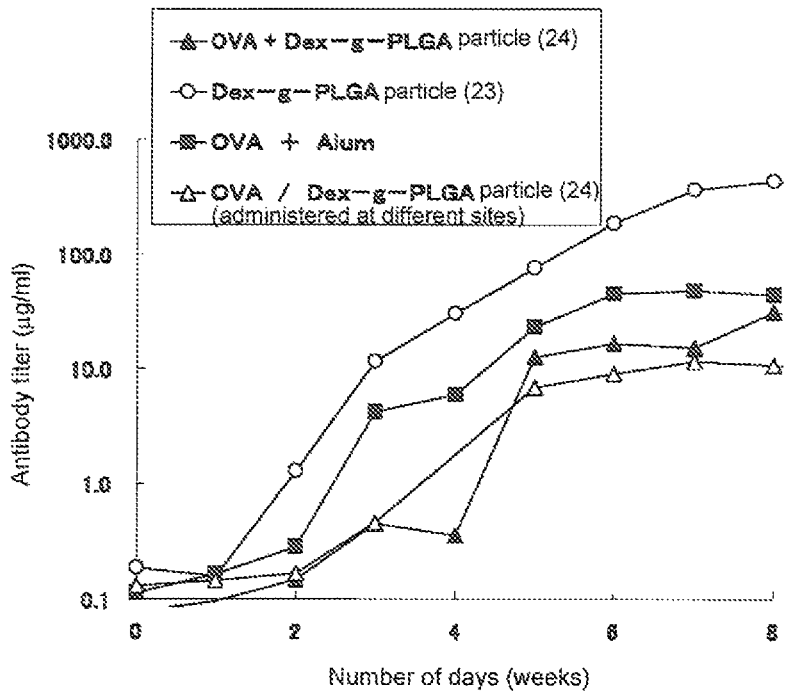
FIG. 9 shows immunological evaluation 4 of OVA-containing immunogenic compositions.

The evaluation was carried out by the same method as in Example 9. The dose per administration was 20 µg in terms of the amount of the antigen in all the cases, and the antigen was administered a total of 3 times at Week 0, Week 2 and Week 4. The evaluation was carried out by comparison among the case where a mixture of 20 µg of OVA and the Dex-g-PLGA particle (24) containing no antigen (16 mg in terms of the polymer amount) was administered, the case where the Dex-g-PLGA particle (23) containing 20 µg of OVA (16 mg in terms of the polymer amount) was administered, the case where a mixture of 20 µg of OVA and 50 µl of Alum was administered, and the case where 20 µg of OVA and the Dex-g-PLGA particle (24) containing no antigen were administered at different sites. The antibody titer in blood was measured by the same method as in Example 9. Under each condition, the administration was carried out for 2 individuals of mice. FIG. 9 shows the average value of the antibody titer.

Results

All the particles showed the antibody titer-increasing effect. The OVA-encapsulating associated particle (Dex-g-PLGA particle (23)) showed a higher antibody titer-increasing effect compared to the case where the mixture of OVA and the particle (Dex-g-PLGA particle (24)) containing no antigen was administered, and the case where OVA and the Dex-g-PLGA particle (24) were administered at different sites.

Example 14

Subcutaneous Administration of CEA-Containing Immunogenic Composition to Mice (4)

Method

Figure 10:
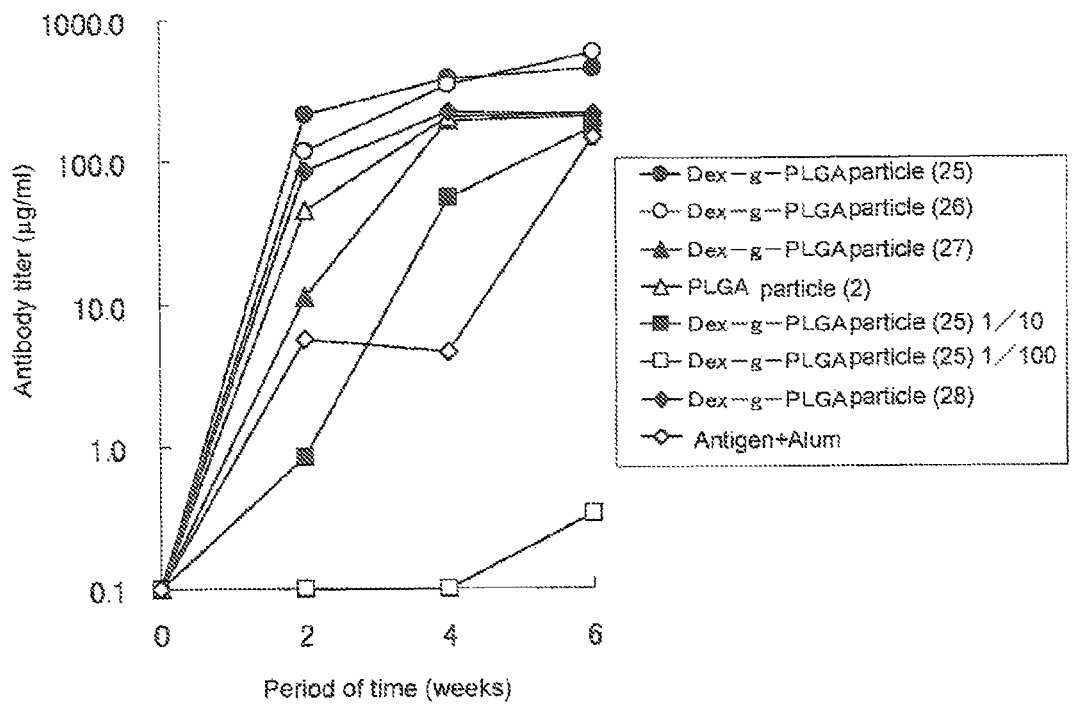
FIG. 10 shows immunological evaluation 4 of CEA-containing immunogenic compositions.
Figure 11:
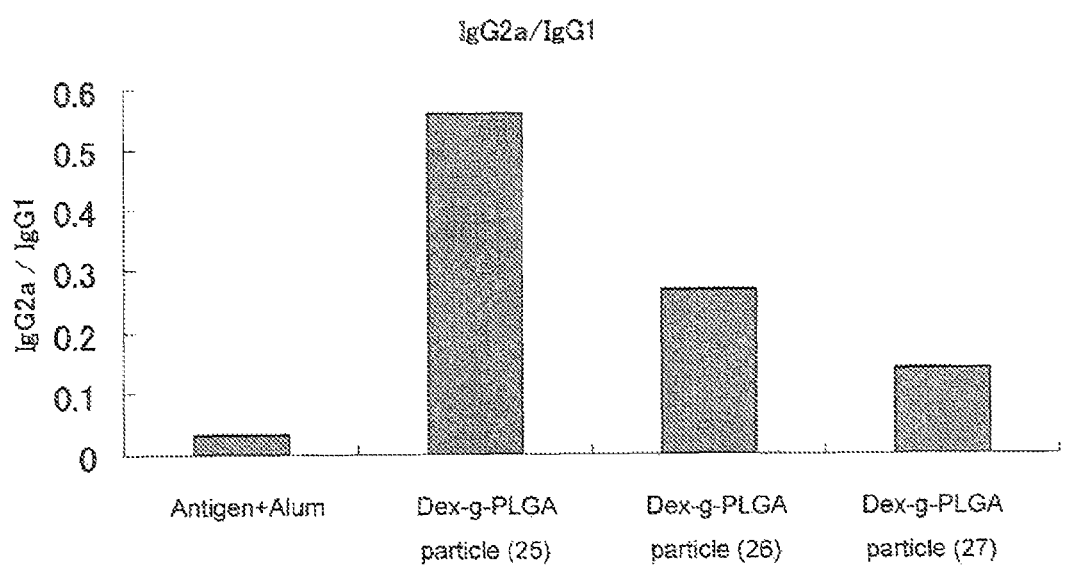
FIG. 11 shows immunological evaluation (IgG2a/IgG1 ratio) of CEA-containing immunogenic compositions.

The evaluation was carried out by the same method as in Example 7. Only in the case where a mixture of CEA and Alum was administered, a total of 3 times of administration was carried out at Week 0, Week 2 and Week 4, and in the other cases where the CEA-encapsulating particles and CEA-encapsulating associated particles were administered, single administration was carried out at Week 0. The evaluation was carried out by comparison among particles which were prepared using the same polymer but have different particle sizes: Dex-g-PLGA particle (25) (particle size, 0.4 µm; polymer content, 4 mg; amount of administration of antigen, 10 µg), Dex-g-PLGA particle (26) (particle size, 5 µm; polymer content, 4 mg; amount of administration of antigen, 10 µg), Dex-g-PLGA particle (27) (particle size, 40 µm; polymer content, 4 mg; amount of administration of antigen, 10 µg), and Dex-g-PLGA particle (28) (particle size, 0.4 µm; polymer content, 4 mg; amount of administration of antigen, 1 µg). Further, in terms of the Dex-g-PLGA particle (25), comparisons were made with the cases where the amount of administration was reduced to 1/10 (polymer content, 400 µg; amount of administration of antigen, 1 µg) or 1/100 (polymer content, 40 µg; amount of administration of antigen, 0.1 µg). As a Comparative Example, the PLGA particle (2) prepared by encapsulation of CEA was evaluated. Under each condition, the administration was carried out for 6 individuals of mice, and the antibody titer, IgG1 and IgG2a in blood were measured by the same method as in Example 7. FIG. 10 and FIG. 11 show the average values.

Results

The CEA-encapsulating particles (Dex-g-PLGA particles (25) and (26)) having an average particle size of 0.4 μm and an average particle size of 5 μm showed higher antibody titer-increasing effect compared to the CEA-encapsulating particle (Dex-g-PLGA particle (27)) having an average particle size of 40 μm. Although the Dex-g-PLGA particle (25) showed a high antibody titer-increasing effect, reduction of it amount of administration to 1/10 or 1/100 resulted in decrease in the antibody titer-increasing effect, and in the case where the amount of administration of the particle was 1/100, only a low antibody titer-increasing effect could be obtained. Comparison between the administration of the Dex-g-PLGA particle (25) in an amount of 1/10 and the administration of the Dex-g-PLGA particle (28), in both of which the amount of the antigen administered was 1 μg, showed that administration of a larger amount of the polymer results in a higher antibody titer-increasing effect (FIG. 10).

Further, for blood at Week 6, the IgG2a antibody titer was measured by the same method as in Example 7, and the IgG1 antibody titer was measured by the same method as in the measurement of the IgG2a antibody titer using an IgG1 antibody. According to measurement of the ratio between these, administration of a mixture of Alum and the antibody resulted in a low IgG2a/IgG1 value, while administration of the Dex-g-PLGA particle (25), (26) or (27) resulted in a high IgG2a/IgG1 value, showing a tendency that a smaller particle size results in a higher IgG2a/IgG1 value (FIG. 11).

Industrial Applicability

The immunogenic composition can be used as a vaccine for therapy and/or prophylaxis of infectious diseases, cancer and the like.

The invention claimed is:

1. A method comprising administering an effective amount of an immunogenic composition comprising an antigen-adjuvant microparticle complex containing an antigen encapsulated in an adjuvant microparticle composed of an amphiphilic graft copolymer(s) comprising a poly(hydroxyl acid) as a hydrophobic graft segment and a polysaccharide as a hydrophilic backbone segment, wherein the number of poly(hydroxyl acid) graft chains of the amphiphilic graft copolymer is 2 to 50, to a living body, and inducing an immune response in the living body.

2. The method according to claim 1, comprising as an effective ingredient a particle composed of said antigen-adjuvant microparticle complex associated together.

3. The method according to claim 1, wherein said adjuvant microparticle has a hydrophilic portion in the inside thereof, said hydrophilic portion being composed of a hydrophilic segment of said amphiphilic polymer, and has an outer layer composed of a hydrophobic portion constituted by said hydrophobic segment of said amphiphilic polymer.

4. The method according to claim 1, wherein said polysaccharide is dextran.

5. The method according to claim 1, wherein said poly(hydroxy acid) is a poly(lactic-co-glycolic acid).

6. The method according to claim 1, further comprising a surface modifier bound to said poly(hydroxy acid) of said adjuvant microparticle.

7. The method according to claim 1, wherein the average particle size of said antigen-adjuvant microparticle complex or said particle composed of said antigen-adjuvant microparticle complex associated together is 0.1 to 50 μm.

8. The method according to claim 1, further comprising an immune-activating substance as an effective ingredient.

9. The method according to claim 8, wherein said immune-activating substance is a nucleic acid.

10. The method according to claim 8, wherein said immune-activating substance is CpG.

11. The method according to claim 9, wherein said immune-activating substance is CpG.

12. The method according to claim 2, wherein said adjuvant microparticle has a hydrophilic portion in the inside thereof, said hydrophilic portion being composed of a hydrophilic segment of said amphiphilic polymer, and has an outer layer composed of a hydrophobic portion constituted by said hydrophobic segment of said amphiphilic polymer.

13. The method according to claim 2, wherein said poly(hydroxy acid) is a poly(lactic-co-glycolic acid).

14. The method according to claim 3, wherein said poly(hydroxy acid) is a poly(lactic-co-glycolic acid).

15. The method according to claim 4, wherein said poly(hydroxy acid) is a poly(lactic-co-glycolic acid).

16. The method according to claim 2, further comprising a surface modifier bound to said poly(hydroxy acid) of said adjuvant microparticle.

17. The method according to claim 3, further comprising a surface modifier bound to said poly(hydroxy acid) of said adjuvant microparticle.

18. The method according to claim 1, wherein said inducing the immune response is vaccination or prevention in a living body of infectious diseases or cancer.

19. A method of inducing an immune response in a cell comprising applying an effective amount of composition comprising an antigen-adjuvant microparticle complex containing an antigen encapsulated in an adjuvant microparticle composed of an amphiphilic graft copolymer(s) comprising a poly(hydroxyl acid) as a hydrophobic graft segment and a polysaccharide as a hydrophilic backbone segment, wherein the number of poly(hydroxyl acid) graft chains of the amphiphilic graft copolymer is 2 to 50, to a living body.

* * * * *